(12) United States Patent
Barfield

(10) Patent No.: US 9,402,568 B2
(45) Date of Patent: Aug. 2, 2016

(54) METHOD AND SYSTEM FOR DETECTING A FALL BASED ON COMPARING DATA TO CRITERIA DERIVED FROM MULTIPLE FALL DATA SETS

(75) Inventor: James R. Barfield, Atlanta, GA (US)

(73) Assignee: Verizon Telematics Inc., Atlanta, GA (US)

( * ) Notice: Subject to any disclaimer, the term of this patent is extended or adjusted under 35 U.S.C. 154(b) by 568 days.

(21) Appl. No.: 13/598,534

(22) Filed: Aug. 29, 2012

(65) Prior Publication Data

US 2013/0054180 A1 Feb. 28, 2013

Related U.S. Application Data

(60) Provisional application No. 61/528,691, filed on Aug. 29, 2011.

(51) Int. Cl.
*G01L 7/00* (2006.01)
*A61B 5/11* (2006.01)
*G08B 21/04* (2006.01)
*G01P 15/08* (2006.01)
*G01L 9/00* (2006.01)

(52) U.S. Cl.
CPC ........... *A61B 5/1117* (2013.01); *G01P 15/0891* (2013.01); *G08B 21/043* (2013.01); *G08B 21/0446* (2013.01)

(58) Field of Classification Search
CPC .................................................. G01P 15/0891
USPC ................................. 702/138, 141, 150, 182
See application file for complete search history.

(56) References Cited

U.S. PATENT DOCUMENTS 7,318,170 B2 * 1/2008 Makela et al. .................. 714/22
2007/0030159 A1 * 2/2007 Stoev et al. .................... 340/669

* cited by examiner

*Primary Examiner* — Phuong Huynh

(57) ABSTRACT

A device monitors sensor data generated by movement of a wearer and determines whether the data indicates a fall. The device may include accelerometers, barometer(s), and sensors that detect, light, sound, temperature, magnetic and electric fields, strain-force on the device, and other environmental conditions. A processor determines whether the data meets a first criterion for a parameter (i.e., exceeding an acceleration or barometric pressure maximum threshold). The first criterion corresponds to a first set of known-fall event data sets. If the first criterion is met, the processor generates a full indication. If the data does not meet the first criterion, the processor compares the data to a second criterion for the same, or different, parameter. If the second parameter is met, further processing confirms a fall determination by comparing the data to other criteria corresponding to known-fall event data sets that differ from the first set.

17 Claims, 16 Drawing Sheets

METHOD AND SYSTEM FOR DETECTING A FALL BASED ON COMPARING DATA TO CRITERIA DERIVED FROM MULTIPLE FALL DATA SETS

CROSS REFERENCE TO RELATED APPLICATION

The present application claims priority under 35 U.S.C. 119(e) to U.S. Provisional Patent Application No. 61/528,691 filed on Aug. 29, 2011, entitled "Method and system for detecting a fall based on multiple fall signature sets," which the present application incorporates by reference in its entirety.

FIELD

The invention relates to fall detection, in particular, wearable, or other mobile devices with wireless communication capabilities for determining and reporting that a fall has occurred.

SUMMARY

A method runs on a processor of a device for monitoring movement of a wearer and for determining whether the wearer has fallen. The device includes accelerometers, barometer(s), and optionally other sensors that detect, among other environmental conditions, light, sound, temperature, magnetic and electric fields, strain-three on the device. The processor determines whether sensor data meets a first criterion for a parameter (such as whether the data exceeds an acceleration or barometric pressure maximum, or threshold). If so, the processor generates an indication that the wearer fell. If the data does not meet the first criterion, the processor compares the data to a second criterion for the same, or different, parameter. For example, the first criterion could be a maximum acceleration wherein data that exceeds it indicates a fall, and the second (or a subsequent criterion if more than two stages of analysis, or evaluation, are performed) may be an orientation change parameter or a barometric change parameter. The first criterion corresponds to a first set of data sets resulting from known fall events. If the second parameter is met, further processing of the data refines the determination that the wearer fell. Further processing can include comparing the data to other criterion corresponding to fall event data sets categorized in a second set of fall data sets that differs from the first fall data set. Reference herein to analysis/evaluation of data with criteria for a fall data set may also be made by referring to evaluation/analysis using a criterion, or criteria, resulting from characteristic segmentation of empirical fall data. Characteristic segmentation refers to evaluating a plurality of event data sets known to have been generated by a fall event, and assigning each fall event data set to a segment wherein the data sets in a given segment have similar characteristics with respect to impact magnitude, free fall duration, transition from non-movement to free-fall (typically based on duration of transition or slope of magnitude change during the transition to free-fall). Fall event data of a given characteristic segmentation having distinguishing characteristics such as impact magnitude, freefall duration before impact, orientation change during free-fall, can be collectively analyzed to generate corresponding criterion, or criteria. If data from a given wearer's movement event does not match one criterion, or criteria, for a particular characteristic segmentation, it may meet criteria for another characteristic segmentation. Thus, data monitored by a device can be compared to multiple criteria corresponding to respective multiple characteristic segmentations depending on the outcome of evaluation vis-à-vis a different characteristic segmentation and thus reliably provide an indication that a wearer fell while reducing the erroneous indication that a wearer has fallen. In addition, if analysis vis-à-vis multiple characteristic segmentations indicates that a fall has not occurred, but nevertheless the analysis of data according to one, or more, criteria corresponding to the characteristic segmentation of fall signature data sets was very close to the criteria, a service provider may receive such analysis and send a request for continuation by the wearer that he, or she, has in fact not fallen. Such indication may be accomplished by pushing a button, or sequence of button presses, of the device. The wearer may respond verbally to a call from the service provider. The user/wearer can configure a preferred method for confirming a fall has not occurred or has occurred.

One embodiment includes a device running a method for detecting falls, comprising a processor configured for: loading a first acceleration magnitude threshold value from a memory; loading a second acceleration magnitude threshold value from a memory; sampling acceleration information from an acceleration measuring means of the device at a predetermined sample rate into sampled acceleration data; storing the sampled acceleration data into a memory capable of storing a predetermined number of sampled acceleration data; determining a calculated magnitude acceleration value from the acceleration data for each sample; comparing the calculated magnitude acceleration value to the first acceleration magnitude threshold value for each sample; comparing the calculated magnitude acceleration value to the second acceleration magnitude threshold value if the calculated magnitude acceleration value does not exceed the first acceleration magnitude threshold value, wherein the first acceleration magnitude threshold value corresponds to a first category of fall signatures and the second acceleration magnitude threshold value corresponds to a second category of fall signatures; and outputting a signal indicating that a fall may have occurred if the calculated magnitude exceeds either the first or the second acceleration magnitude thresholds.

The processor of the device may be further configured for sampling orientation information from an orientation measuring means of the device; determining a change in orientation of the device between a time corresponding to a sample where the calculated magnitude acceleration value exceeded either of the first or the second acceleration magnitude thresholds and a time corresponding to a sample that precedes the sample where the calculated magnitude acceleration value exceeded either of the first or the second acceleration magnitude thresholds by the predetermined number of samples; outputting a signal indicating that a fall may have occurred if the determined change in the orientation of the device exceeds a predetermined orientation threshold; and wherein the predetermined orientation threshold corresponds to one of the first or second acceleration magnitude thresholds, and wherein the predetermined orientation threshold has a different value if it corresponds to the first predetermined acceleration magnitude threshold than if it corresponds to the second predetermined acceleration magnitude threshold.

The processor may be further configured for sampling orientation information from an orientation measuring means of the device; determining a change in orientation of the device between a time corresponding to a sample where the calculated magnitude acceleration value exceeded either of the first or the second acceleration magnitude thresholds and a time corresponding to a sample that precedes the sample where the calculated magnitude acceleration value exceeded either of the first or the second acceleration magnitude thresholds by the predetermined number of samples; outputting a signal indicating that a fall may have occurred if the determined change in the orientation of the device exceeds a predetermined orientation threshold; and wherein the predetermined orientation threshold corresponds to one of the first or second acceleration magnitude thresholds, and wherein the predetermined orientation threshold has the same value regardless of whether it corresponds to the first predetermined acceleration threshold value or to the second predetermined acceleration threshold value if the first predetermined acceleration threshold value and the second predetermined acceleration threshold value are substantially the same.

Each acceleration information sample may include acceleration magnitudes for three axes, and the processor may determine for each sample the calculated magnitude acceleration value by calculating the square root of the sum of the squares of the three acceleration magnitudes.

In another embodiment, a device for detecting falls comprises: a processor configured for: loading a first acceleration magnitude threshold value and a second acceleration magnitude threshold value from a memory; sampling acceleration information from an acceleration measuring means of the device at a predetermined sample rate into sampled acceleration data; determining a calculated magnitude acceleration value from the acceleration data for each sample; storing the calculated magnitude acceleration values into a memory capable of storing a predetermined number of calculated magnitude acceleration values corresponding a predetermined number of samples of acceleration data; comparing each calculated magnitude acceleration value to the first acceleration magnitude threshold value; evaluating the predetermined number of calculated magnitude accelerations values to determine a number of free-fall occurrences, wherein a calculated magnitude acceleration value that does not exceed the second acceleration magnitude threshold value indicates a free-fall occurrence, and wherein the predetermined number of calculated magnitude values corresponds to samples of acceleration data that occurred before a calculated magnitude acceleration value exceeded the first acceleration magnitude threshold value; comparing the number of free-fall occurrences to a free-fall limit value, wherein the free-fall limit value is determined from empirical fall data; and outputting a signal indicating that a fall may have occurred if the number of free-fall occurrences does not exceed the free-fall limit value. The predetermined fall evaluation period may be a predetermined amount of time. The predetermined fall evaluation period may also be a predetermined number of samples.

The device may compare data it acquires with empirical fall data where the first acceleration magnitude threshold value, the second acceleration magnitude threshold value, and the free-fall limit value correspond to one of a plurality of sets of empirical fall data.

In yet another embodiment, a device for detecting falls comprises: a processor configured for: loading a first acceleration magnitude threshold value and a second acceleration magnitude threshold value from a memory; sampling acceleration information from an acceleration measuring means of the device at a predetermined sample rate into sampled acceleration data; determining a calculated magnitude acceleration value from the acceleration data for each sample; evaluating calculated magnitude accelerations values to determine a number of free-fall occurrences that occur after a first free-fall occurrence, wherein the first free-fall occurrence corresponds to a calculated magnitude acceleration value that does not exceed the second threshold; comparing the number of free-fall occurrences to a free-fall limit value, wherein the free-fall limit value is determined from empirical fall data; comparing each calculated magnitude acceleration value to the first acceleration magnitude threshold value; and outputting a signal indicating that a fall may have occurred if the number of free-fall occurrences does not exceed the free-fall limit value during a predetermined fall evaluation period that begins at, or after, the first free-fall occurrence and ends when a calculated magnitude acceleration value exceeds the first threshold.

The predetermined fall evaluation period may be a predetermined amount of time. The predetermined fall evaluation period may also be a predetermined number of samples.

The device may compare data it acquires with empirical fall data where the first acceleration magnitude threshold value, the second acceleration magnitude threshold value, and the free-fall limit value correspond to one of a plurality of sets of empirical fall data.

An additional embodiment includes fall data criteria determined from a first set of fall data determined by a method that comprises the steps of: descending with a device that includes an accelerometer means, a processor, and communication means; acquire acceleration data from the accelerometers; and evaluating the acceleration data to determine at least one of a plurality of baseline fall criteria corresponding to at least one of a plurality of fall parameters.

In determining the fall data, the act of descending may comprise a simulated fall. The act of descending may also comprise an actual fall. The act of descending may also comprise a drop. The baseline fall criteria may include a first acceleration magnitude threshold, a second acceleration magnitude threshold, a free-fall limit value, an orientation change maximum, fall evaluation period value. The fall data criteria may be determined from multiple sets of data corresponding to multiple acts of descending.

The fall data criteria may be further determined by evaluating a second set of fall data that includes less that all of the data included in the first set of fall data to determine a first modified criterion corresponding to a first one of the at least one of a plurality of fall parameters, wherein the second set of fall data does not include acceleration data corresponding to a plurality of acts of descending that meet the baseline criterion corresponding to the first one of the plurality of fall parameters.

Another embodiment may also include a device for detecting falls that comprises: a processor configured for: loading an acceleration magnitude threshold value and an integration threshold value from a memory; sampling acceleration information from an acceleration measuring means of the device at a predetermined sample rate into sampled acceleration data; determining a calculated magnitude acceleration value from the acceleration data for each sample; storing the calculated magnitude acceleration values into a memory capable of storing a predetermined number of calculated magnitude acceleration values corresponding a predetermined number of samples of acceleration data; comparing each calculated magnitude acceleration value to the first acceleration magnitude threshold value; evaluating each of the predetermined number of calculated magnitude accelerations values by integration to result in a corresponding integration value; storing the integration value; comparing the integration value to the integration threshold value; and outputting a signal indicating that a fall may have occurred if the integration value is less than the integration threshold value.

In another embodiment, a device for detecting falls may comprise a processor configured for: receiving a proximity signal from at least one proximity sensor that outputs the proximity signal that indicates whether an object is within a predetermined distance of the sensor; determining if the device is worn on as body based on an indication from the proximity sensor signal that an object is with the predetermined distance; and enabling at least one other sensor in the device to generate a signal that corresponds to a characteristic that can indicate that a fall has occurred if the processor determines that the device is close to a body.

The device may further comprise an attachment band that includes a first portion and a second portion; the processor further configured for: receiving a fastened signal from an electrical circuit that indicates that an attachment band of the device has been fastened; and outputting a signal to enable fall detection sensors and a corresponding fall detection method to determine whether a fall has occurred if the signal from the electrical circuit indicated that the attachment band is fastened. The electrical circuit may include a circuit for measuring impedance. The electrical circuit may include a circuit for measuring current. The electrical circuit may include a circuit for measuring voltage between the first portion and the second portion. Each of the first and second portions may include an electrical conductor configured to couple with the electrical conductor of the other portion. At least one of the first and second portions may be formed at least partially from a non-conducting flexible material. At least one of the portions may include a plurality of contacts coupled to the electrical conductor of the at least one of the portions.

Alternatively, the device may further comprise an attachment band that includes a first portion and a second portion; wherein the proximity sensor is attached to one of the first and second portions for detecting when the first and second portions are proximate one another, and wherein the proximity sensor outputs a fastened signal that indicates that the attachment band of the device has been fastened when the proximity sensor detects that the first and second portions are proximate; and wherein the processor is further configured for outputting a signal to enable fall detection sensors and a corresponding fall detection method to determine whether a fall has occurred if the signal from the proximity sensor indicated that the attachment band is fastened.

In another embodiment, a device for detecting falls comprises: an attachment band that includes a first portion and a second portion; a processor configured for: receiving a fastened signal from an electrical circuit that indicates that an attachment band of the device has been fastened; and outputting a signal to enable fall detection sensors and a corresponding fall detection method to determine whether a fall has occurred if the signal from the electrical circuit indicated that the attachment band is fastened. The electrical circuit may include a circuit for measuring impedance. The electrical circuit may include a circuit for measuring current. The electrical circuit may include a circuit for measuring voltage between the first portion and the second portion.

In the device, each of the first and second portions may include an electrical conductor configured to couple with the electrical conductor of the other portion. At least one of the first and second portions may be formed at least partially from a non-conducting flexible material. At least one of the portions may include a plurality of contacts coupled to the electrical conductor of the at least one of the portions.

DETAILED DESCRIPTION

Figure 1:
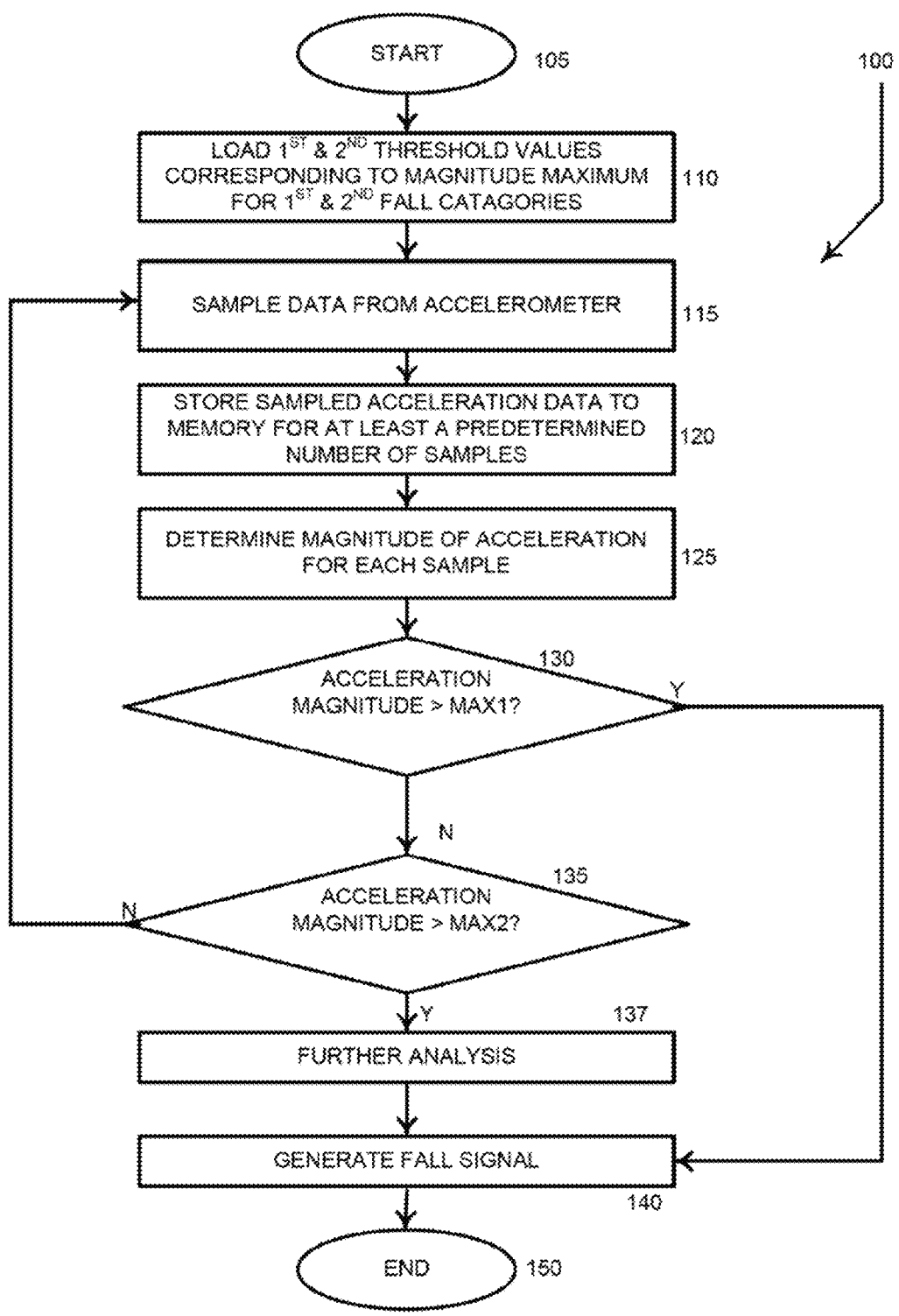
FIG. 1 illustrates a flow diagram of a method for detecting a fall based on exceeding multiple acceleration magnitude thresholds.

Turning now to the drawings, FIG. 1 illustrates a method 100 for detecting that a fall has occurred based on an acceleration magnitude. The values used for determining the acceleration magnitude may come from sensors, such as accelerometers, gyroscopes, barometers, or other similar sensors that can detect physical characteristics that relate to a change in position of a device that includes the sensor. For example, personal, wearable, devices that attach to clothing, or otherwise can be attached to a person, or object, may include wireless communication processor circuitry and global positioning satellite processor ("GPS") circuitry. In addition the personal wearable device (may be referred to hereinafter as "fall device") may include sensors and transducers, such as single, or multiple-axis, accelerometers, barometers, gyroscopes, heart rate detectors, microphones, speakers, buttons, visual display, and the like, that couple to either, or both, of the wireless communication processor circuitry and the GPS circuitry. When referring herein to either of the wireless processor circuitry or GPS processor circuitry, each typically include an integrated circuit, supporting circuitry such as A/D and D/A, memory, power supply circuitry, discrete components, and other items such as antennas, amplifiers, buffers, registers, etc. Typically, one of the processors (usually the wireless communication processor) performs most of the general processing of the device in addition to its specific duties related to core function (e.g., wireless communication processing). However, processing duties may be distributed among multiple processors. For example, an auxiliary processor may handle power management for all components of the full device, and the GPS and communication processor may handle higher level processing duties. Unless otherwise noted, reference herein to a processor means the higher level processing, which may, or may not, include a given processor's core role functionality.

Continuing with the description of FIG. 1, method 100 begins at step 105. At step 110, the processor of the fall detection device retrieves values stored in a memory for use in comparing to measured acceleration values. The retrieved values include a plurality of acceleration magnitude threshold values. The threshold values correspond to magnitude values determined from evaluation of a plurality of empirically obtained data sets. The data sets include sampled acceleration data from an accelerometer sensor (a sensor can include one, two, or three actual accelerometers corresponding to one, two, or three axis of motion). Preferably, data from data sets corresponding to very many descent events should be evaluated. Evaluating and analyzing data from the multiple descent events typically results in categorization of the data sets, or signatures, into categories, in which signatures in each category share common, or similar characteristics. The fall signature of a person wearing a fall device while falling due to sudden unconsciousness may have different characteristics than the signature of a person wearing a fall device who falls due to a sudden loss of balance. Other categories of fall signatures may include falling due to tripping, falling from a chair, falling from a wheel chair, falling while grasping for a support, amount others. A descent event that may seem like a fall is the act of tossing a fall device onto a floor, shelf, desktop, etc. A toss event typically exhibits a longer period of zero acceleration (corresponding, to free fall) than a person who falls. A conscious falling person typically tries to steady himself, brace himself against a wall or furniture, or otherwise arrest the fall. A suddenly unconscious person cannot try to mitigate the fall, but nevertheless typically changes orientation as the body descends compared to a toss event, which typically has a longer uninterrupted, minimal orientation-changing, free fall period.

Different categories of fall signatures may, and typically do, have different peak acceleration magnitude spikes that correspond to the device (whether from a toss or actual fall) suddenly decelerating when the fall event ends. An acceleration magnitude threshold value for each of multiple categories is typically chosen high enough to avoid false positives (i.e., from a toss event) but low enough to capture a likely falls based on the empirical data sets for the given category. Moreover, the acceleration magnitude threshold value for a given category can be lower when other factors, in addition to acceleration magnitude, are evaluated as a potential fall event. For example, based on empirically gained knowledge that a trip event typically has a shorter free-fall period, with a relatively high orientation change, followed by a lower magnitude spike as compared to a toss event, with the time between the free fall period and magnitude spike is longer than a toss event, the predetermined magnitude threshold for a trip category can be set lower than for a toss event category. However, to reduce false positive determinations, the change in orientation, the rate of descent (e.g., from evaluating barometer sensor data) and free fall period, can be compared to a predetermined orientation limit, a predetermined rate of descent limit, and a predetermined free fall period threshold, respectively. One skilled in the art will appreciate that the terms 'threshold' and 'limit' typically refer to values that when current date is compared against trigger an action, or cessation of action, respectively, that establishes an accepted operating range. The terms may be used interchangeably herein, but generally a measured value that exceeds a threshold, e.g., a measured magnitude spike value exceeding a predetermined value that corresponds to a fall device impacting a surface after descending for a period indicates the likelihood of an impact. On the other hand, for an acceleration signature of a potential fall event, if the time between a point that a measured acceleration value exceeds a maximum (sudden stop of descent) threshold value and an earlier-occurring point that a measured acceleration value dropped below a free-fall threshold value are within a predetermined time limit, then the signature may indicate as fall. Or, if for an acceleration signature of a potential fall event the period that acceleration magnitude values stay below a free fall threshold exceeds a predetermined free-fall limit, then an evaluation of the potential fall signature may indicate a toss event since the free-fall period was longer than the predetermined limit—a shorter period of free-fall may indicate a fall device wearer tried to break his, or her, fall.

Thus, the threshold values loaded at step 110 typically include first and second threshold value for at least two different fall categories. For purposes of discussion, assume the processor loads values for two different fall categories one and two. For each category, a first acceleration magnitude threshold corresponds to a peak magnitude typically associated with sudden deceleration that occurs when a fall device ceases descending. A second acceleration magnitude threshold corresponds to a value that indicates a free fall when the acceleration magnitude output signal of the fall device is below it. One skilled in the art will appreciate that a magnitude value, whether predetermined from calculation from a data set for an empirical fall event, or from real-time monitoring for comparison to the predetermined calculated value, the value can be a direct reading (after applying calibration coefficients) if the acceleration measuring device is a single-axis device. Or, if the acceleration device is a more typical three-axis acceleration measuring device, the calculation of the magnitude my include performing a square root sum of the squares operation on the three values from the three accelerometer components sampled simultaneously.

Continuing with the discussion of FIG. 1, the processor in the fall device samples data from an acceleration measuring means at step 115 and stores the sampled data to a memory at step 120. The memory allocated for storing the real-time sampled data is preferably a predetermined amount—when the memory has stored the predetermined number of samples, the oldest is discarded to make room for the next one— according to a first in first out routine ("FIFO"). For each stored sample of acceleration data, the processor calculates a magnitude value at step 125.

At step 130, the processor determines whether the calculated magnitude for a given sample exceeds a first acceleration threshold. Preferably, the first acceleration magnitude threshold is a maximum value derived from fall data corresponding to a given first fall category, or characteristic segmentation fall data set. If a calculated acceleration magnitude exceeds the threshold, the processor outputs a signal at step 140 indicating that a fall may have occurred. If the processor determines at step 130 that the current sample's calculated magnitude does not exceed the first threshold, it compares the calculated magnitude to a second threshold at step 135. The second threshold corresponds to a maximum magnitude derived from a second category of fall data which is different than the data set used to determine the acceleration threshold for the first category of fall data. Preferably, the first magnitude threshold is greater than the second. If the calculated magnitude of data for the current sample of data exceeds the second threshold, the processor performs further analysis at step 137, which can include methods discussed in greater detail in reference to FIG. 2. After performing the further analysis, if the processor determines that a fall has occurred, it generates a signal at step 140 indicating that a fall may have occurred. It will be appreciated that the further analysis may include determining free fall period length by analyzing accelerometer magnitude signal samples, frequency analysis (i.e., Fast Fourier Transform) of accelerometer signals (either on individual signals corresponding to a given axis or on the magnitude of all axes). The processor can perform various statistical functions on the data further analyzed, including integrating the acceleration magnitude signal during a free fall period, integrating the acceleration signal during a high acceleration event portion of the signal, determining a standard deviation of the acceleration signals to distinguish between different typical behaviors, such as walking, running, sitting, lifting, and falling. Similarly, determining a mean of the acceleration signal, or signals, can distinguish between different activities. Thus, even if the acceleration magnitude signal exceeds the second threshold, the further analysis can reduce the likelihood of erroneously outputting a signal indicating at fall if the further analysis indicates an activity other than a fall, which may not require assistance of emergency personnel or resources.

The further analysis may include comparing the determined integrals, means, medians, averages, standard deviations, Fourier analysis, and other statistical results, to corresponding criteria to determine whether an event having an acceleration magnitude that exceeds the second threshold may not be a fall.

The processor may be configured to generate a fall signals as a fall alert—i.e., sending a message via e-mail, SMS, voice call, etc. that the wearer assigned to the fall device may have fallen. Method 100 ends at step 150.

Figure 2:
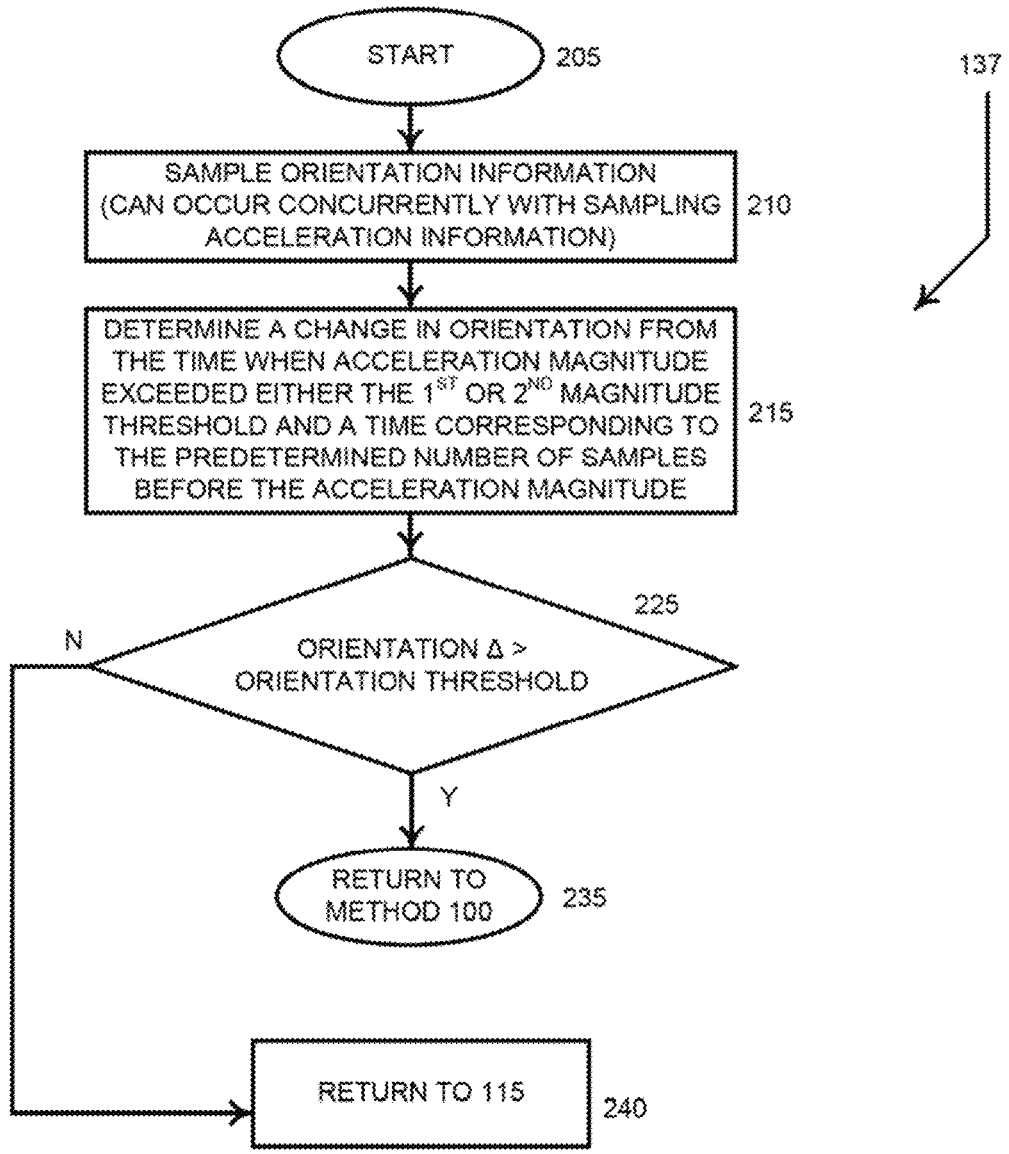
FIG. 2 illustrates a flow diagram of a method for detecting a fall based on a change in orientation value.

Turning now to FIG. 2, the figure illustrates a method 137 for further refining the determination that a fall occurred after acceleration data for a given sample exceeded a predetermine acceleration magnitude threshold. Method 137 begins at step 205 when method 100 reaches step 137. At step 210, the processor calculates a determination of the orientation of a given sample, either as it is sampled or after it is stored as one of the predetermined number of samples of data. The orientation can include determining angle of orientation of the fall device based on acceleration component signals from the accelerometer sensing means, e.g., a three-axis accelerometer device. In addition, signals from barometers or gyroscopes can be used to enhance the orientation calculation based on acceleration data. At step 215, the processor determines a change in orientation value, or angle, between the sample where the magnitude exceeded the acceleration magnitude threshold at step 135 shown in FIG. 1, (for purposes of discussion this sample is referred to as the magnitude spike sample) and the sample (or samples if an average is used) contained in the predetermined number of samples before the spike sample. (It will be appreciated that the further analysis may be performed after a comparison of accelerometer values to a magnitude threshold value at step 130 results in following the 'Y' path therefrom). The processor uses the two orientation values for the determination of an orientation change value. At step 225 the processor makes a comparison to evaluate if the orientation change value exceeds a predetermined orientation change threshold, wherein the orientation change threshold corresponds to the fall data category associated with the threshold value used to determine that the acceleration magnitude spike occurred. If the orientation change value exceeds the orientation change threshold value, method 137 returns at step 235 and the processor generates a fall alert indicating a fall at step 140, shown in FIG. 1. If the processor determines at step 225 that the orientation change value does not exceed the orientation change threshold value, method 137 advances to step 240 and returns to step 115 of method 100.

Classification Based Fall Method

Stage 1 (Initial Conditions of a Potential Fall to Start Processing Based on Zero G and Larger Acceleration Present)

Figure 3:
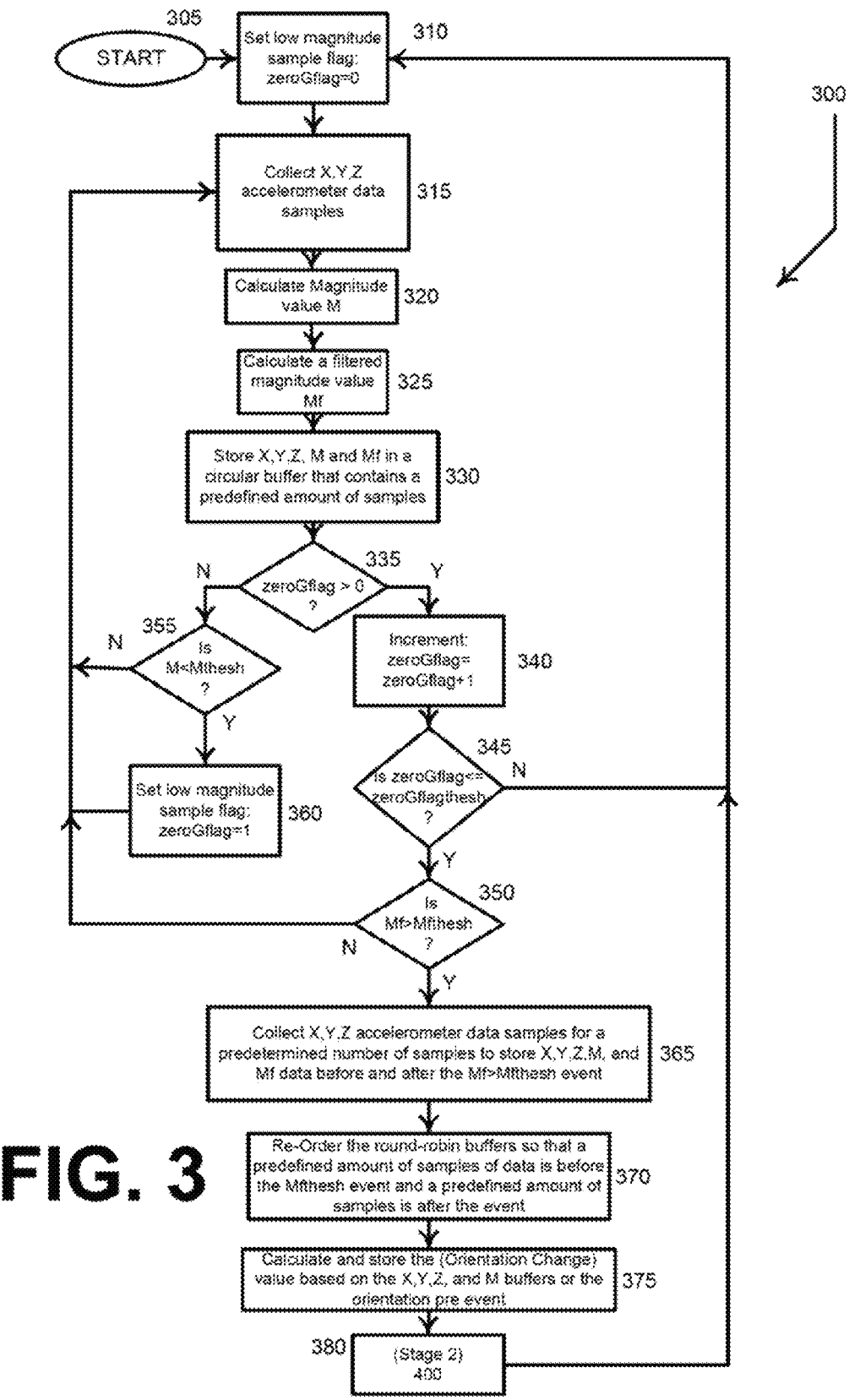
FIG. 3 illustrates stage 1 of a fall detection method that checks accelerometer data for initial indications of a fall.

Turning now to FIG. 3, the figure illustrates method 300 for determining if initial conditions are met to start processing data with a multi-stage fall algorithm. Starting at step 305, referred to as stage 1 and progressing to step 310, a magnitude sample variable (zeroGflag) is set to zero. At step 315, method 300 collects accelerometer data from a 3-axis accelerometer (X, Y, Z) and the magnitude is calculated; at step 320 the method calculates the square root of the sum of the squares of the (X,Y,Z) values. In step 325, a filter attenuates large and quick spikes that typically result from bumping the device (typically using a low pass filter). In step 330, the resulting X, Y, Z, M, and Mf values are then stored in a buffer so that a historical representation of the data is present that is stored in the devices memory. When the method first starts, the buffer is empty; however, as time progresses the circular buffet/FIFO/round robin fills with data as time progresses.

Typical lengths of time for the buffers are 6 to 8 seconds of data. Progressing in the method to step 335, a flag condition is checked to see if zero G force has been detected within a predetermined number of samples. If this is not the case (i.e., zeroGflag is not greater than or equal to zero) then the raw magnitude value M is checked to see if it is below a certain gravity proxy threshold value (shown in step 355) to determine whether free-fall exists. The gravity proxy value corresponds to force due to gravity on a non-moving object, and is preferably selected as less than 1 G to reduce sensitivity to movement and thus reduce false indication of the beginning of a free fall period. In an aspect, 0.7 G provides a good balance between sensitivity to the beginning of free-fall and suppression of false positive indication. However, different values than 0.7 G for the gravity proxy may be used to indicate transition from non-movement to free-fall for differing characteristic segmentations. As with the acceleration magnitude threshold values and free-fall duration limit values, which are determined from evaluation of many event data sets known to correspond to fall events, the gravity proxy may differ for different respective characteristic segmentations (discussed in more detail in reference to FIG. 4). The free-fall duration limit may be referred to herein as a full evaluation period limit value.

At step 360 ZeroGflag is set to 1 so that for subsequent samples of X,Y,Z, data step 335 follows the 'Y' path to determine whether the current Mf sample is greater than the Mfthesh value (threshold values are typically determined empirically from data sets of accelerometer full data taken on the same device) that indicates a large impact when the faller hits the ground. Following the 'Y' path at step 335, zeroGflag is incremented by one at step 340. At step 345, method 300 makes a comparison between zeroGflag and zeroGflagthesh. If zeroGflag is greater than zeroGflagthesh then the method returns to step 310 where ZeroGflag is set to 1 to cause method 300 to follow the 'N' path at step 335. When the zeroGflag is set to 1 following, a return to step 315 from 360, method 300 progresses back to step 335 where the 'Y' path is followed, and on to step 340. At step 345, a counter (comprising steps 340 and 345) resets after a predetermined time, or number of samples as discussed herein, after a 'Y' result at step 355, if zeroGflag attains the predetermined number, or time, before Mi>Mthresh at step 350. At step 345, while the counter is less than the threshold value, the method follows the 'Y' path to step 350. In step 350, the current filtered magnitude sample (Mt) is compared to a filtered magnitude threshold to validate that the peak value is greater than a threshold value. This validation ensures that a free-fall period is followed by a large impact within a predetermined period of time. If the magnitude value is greater than the threshold value then the method progresses to step 365.

In step 365, the processor waits for another predetermined period while the buffers that hold sampled data store incoming accelerometer data after the free fall and large magnitude event occur so that the buffers will include data collected before and after large magnitude event spike for further processing. This data provides access to stored sampled data corresponding to acceleration data corresponding to events occurring before and after the large magnitude spike. Because the data is stored in a circular buffer, the buffer may be reordered so that it contains correctly time-sequenced data buffer as shown in step 370. In step 375, the orientation change of the device is then determined by comparing data stored to the buffer before the large acceleration event with data stored to the buffer after the event. The orientation change is calculated by processing each of the axes' data to determine an amount of orientation change for that given axis of the device from an initial condition (only gravity exerting acceleration on the device) before the free-fall and large spike event typical for fall events to the device's orientation after the event. After determining the orientation change for each axis, the orientation changes for all axes may be summed to result in a summed orientation change, typically given in degrees each axis changes from gravity. Typically, the degree change is observed for all three axes but can be observed for only one or two axes. With the orientation calculation performed, the method progresses to step 380, which progresses to method 400 referred to as stage 2. Then, after method 400 completes and returns to method 300, method 300 advances to step 310 where method 300 restarts.

Stage 2 (Fall Window Classification Portion of the Fall Method)

With stage 1 completed, Stage 2 (shown in FIG. 4) method 400 starts at step 402 after being called from step 380 in FIG. 3. Stage 2 classifies fall events based on different sets of features contained in a fall signal, or fall signature, in one of many different ways. Machine learning techniques separate and classify fall data sets in different ways according to basic characteristics represented in fall signature data sets. Step 402 progresses to step 404 where an index (i) is defined. Index (i) refers to a time that corresponds to the magnitude value sensed in stage 1 when the magnitude value first exceeded the second threshold Mfthesh. In step 406, method 400 retrieves a sample of the filtered magnitude at index (i) in the filtered magnitude buffer of potential fall data. In step 408 for a particular sample, the filtered magnitude is checked to determine whether it lies between two magnitude threshold values. If the retrieved value that represents duration of acceleration magnitude being below ZeroG lies between these two predetermined threshold values then the method progresses to step 410; if not the method progresses to step 418.

Steps 408 through 416 correspond to determining characteristics from retrieved data extracted from a user device and to determining whether to categorize the data as a fall event that has a small amount of free fall and below normal impact magnitude when the faller makes contact with the ground. Criteria for determining whether the characteristics of a potential fall data set are indeed a fall event are shown in the figure as separated into six different types of fall events, but could be separated into more sets of criteria representing different feature sets to define, or to further define, characteristics associated with different types of fall events. Machine learning approaches define segmentations of fall event data sets by associating each of a plurality of empirical event data sets with criteria corresponding to a given segment, and then uses the segmented fall event data sets to determine particular thresholds for the segmented data sets, thus defining the thresholds for the corresponding segment.

Continuing to step 410, the orientation determined in method 300 of the potential fall event data set is evaluated to determine whether it is greater than a predetermined orientation threshold associated with the low-free-fall-duration and low-impact-magnitude category (steps 408-416). If the result of this check is 'Y', the method continues to 412. Otherwise, the method advances to step 418. In step 412, method 400 retrieves a predetermined number of samples of data from the magnitude buffer for the potential fall event wherein the predetermined number of samples is based on the fall signature dates sets for a particular category of fall events. Method 400 causes retrieval of the predetermined number of samples from the buffer that precedes the index (i). Using the data extracted in 412, at step 414 the extracted data is analyzed to determine the number of samples that are below a magnitude threshold value for the low free-fall/low impact category thus indicating a number of samples of free-fall (number of samples having magnitude approximately equal to zero); this number of samples is stored in the variable SampleZG. In step 416, the value stored in SampleZG is evaluated to determine whether it is less than or equal to a threshold value that defines the amount of free-fall for a particular free-fall threshold for the low free-fall/low impact category. Another condition checked in step 416 to determine if SampleZG is greater than zero to ensure that at least some amount of time is spent in free-fall is during the fall that is below the ZeroG threshold corresponding to this characteristic segmentation of fall signatures. If this condition is met, then the method progresses to step 468, where a signal is output to indicate a fall has occurred.

Figure 4:
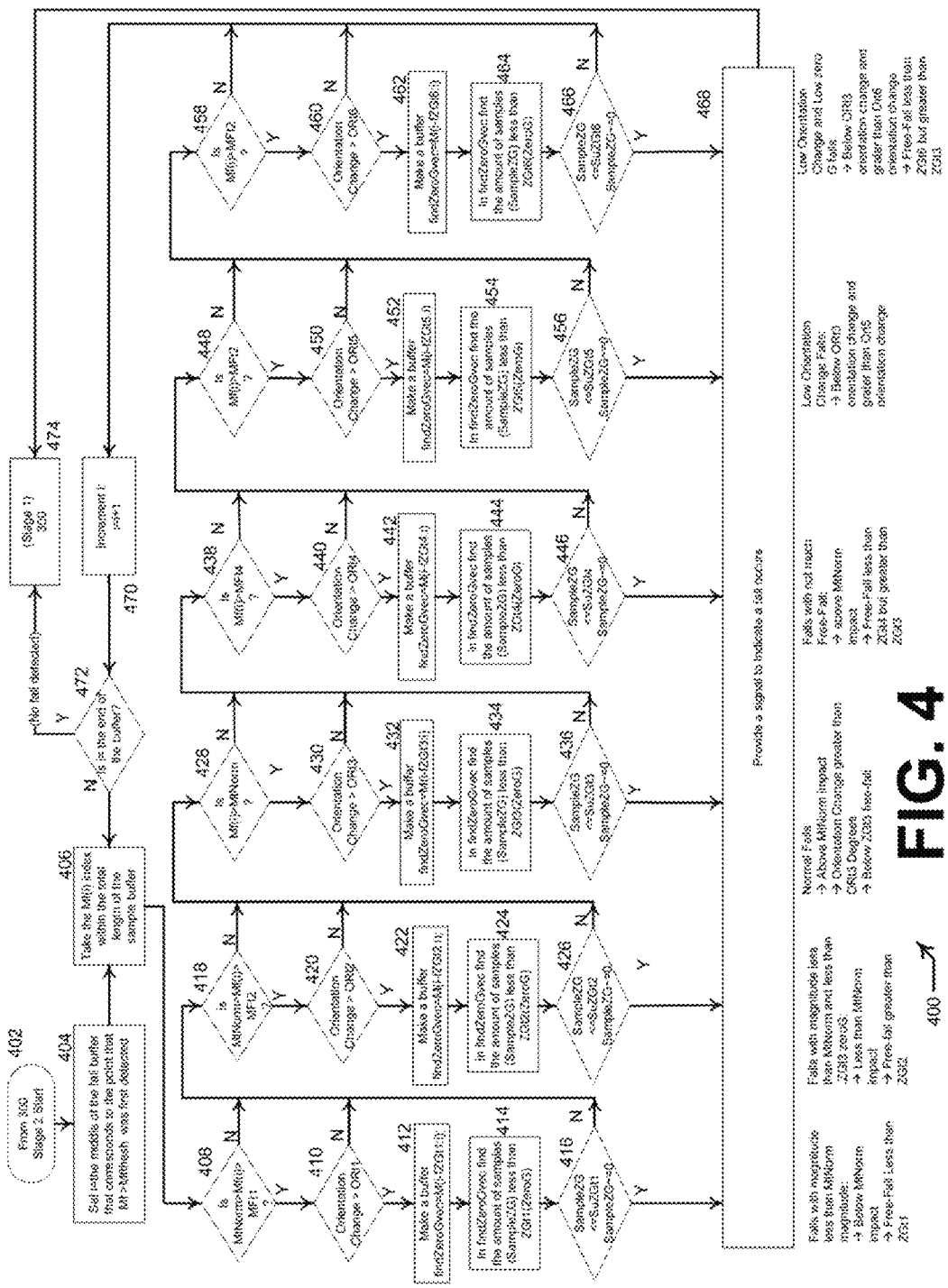
FIG. 4 illustrates stage 2 of a fall detection method that determines if fall occurs based on a window of collected accelerometer data.

Steps 418 through 426 function similarly to steps 408 through 416 but analyze potential fall event data against different predetermined threshold values corresponding to different types of falls (falls with lower magnitude and a higher amount of G force during the free-fall of the fall event) to define a different characteristic segmentation of fall signatures. Again, machine learning methods make the separation between fall signatures in order to define threshold values unique for each fall category. FIG. 4 shows 6 fall types that are represented by the 6 collections of steps (e.g., one collection is indicated by steps 408-416). The number of categories can be larger or smaller depending on how specifically the method configures a processor to classify different types of falls and can be optimized using machine learning techniques.

The categories in method 400 represent the following: Steps 408-416 represent higher G force values contained in the magnitude accelerometer signal than typical free fall (short amount of time spent when the faller is in free-fall before impact with the ground) and lower impact than normal falls (softer impact than most falls when the faller hits the ground). Method 400 identifies a potential fall acceleration data set as a fall if the data indicates a peak magnitude between a range of values, a predetermined amount of free-fall below a threshold that is defined for most fall signature sets of data for this data set and a typical orientation change for all the falls in a data set corresponding to the falls in this category that are taken from a large fall acceleration, data set. The respective magnitude ranges, predetermined number of samples below a predetermined free fall threshold magnitude, and the orientation threshold are determined by statistically grouping empirically determined fall signature data sets that are related by high correlation, grouped by machine leaning methods, or other statistical function.

Steps 418-426 are similar to steps 408-416, also have a characteristic segmentation of falls correspond to falls that have lower impact than typical falls and have a magnitude threshold high cutoff threshold value equal to the value that a typical fall contains. However, when compared to steps 408-416, steps 418-426 have less time spent in free-fall when just prior to the faller making impact with the ground and due to the low amount of free-fall have a lower ZeroG threshold cutoff. Thus, this characteristic segmentation of falls have a low cutoff value that represents the lowest acceleration magnitude value for an impact and a higher magnitude of acceleration period of time that represents the free-fall measured among fall signature data sets in this category. In this category, the empirical fall data sets that result in the acceleration magnitude threshold values for the group have free-fall periods less than a defined threshold value for the data set.

Steps 428-436 correspond to typical fall events. Primary characteristics of this category are events thereof have impact magnitudes typical values for a large data set of fall events, typical free fall and time below the typical free-fall threshold, and typical orientation changes for the falls in the data set taken from a large data set based on the contained criteria. The free-fall magnitude threshold is defined by the fall events in the typical fall data set corresponding to typical falls. From a physical characteristic perspective, these falls typically represent falls where a falling individual ("faller") starts from a vertical position and ends flat in a horizontal position (typical orientation change), a faller starts to reach a period of free-fall where the magnitude of the acceleration is close to zero for a typical amount of time (free fall meets a typical threshold for the data set for a typical amount of time that is defined by normal falls), and the faller has a larger impact with the ground (the magnitude of the acceleration is larger than when a faller lands softly and makes impact with the ground).

Steps 438-446 correspond to discerning falls that have lower acceleration magnitude values for shorter duration during the period of time that represents when a faller experiences free-fall (i.e., a relatively low number of samples having an acceleration magnitude lower than a free-fall threshold that characterizes typical fall events), but contain above-normal acceleration magnitude threshold values when the faller makes impact with the ground and have an orientation calculated determined from empirical data sets otherwise meeting this criteria. The threshold values that identify low free-fall durations in steps 438-446 are determined by identifying empirical fall event data sets with the defined criteria. Machine learning methods provide this separation by choosing falls with a small amount of free-fall duration and how close how close acceleration magnitude approaches zero during transition from approximately 1 G that defines the gravity on an accelerometer.

In steps 448 through 456, method 400 classifies what is defined as low orientation falls. Potential kill data sets that contain an orientation change below a typical fall's orientation change as defined by machine learning methods are used to produce a threshold that identifies a subset of fall data sets from a larger set of fall data sets that define what potential full data sets should be detected by the fall detection method. The characteristic segmentation of fall signatures based on a subset of fall data sets produces an orientation threshold value that indicates whether a potential fall data sets corresponds to a having greater than the lowest orientation change value of the falls that are deemed low orientation falls but is less than typical falls. The corresponding peak magnitude and free-fall threshold values are produced from the subset of fall data. These threshold values create a check in the method that defines falls that contain lower orientation change than a typical fall but have other defining characteristics that distinguish a fall from a non-fall, thus reducing false positives.

Steps 458-466 use the same means to classify falls that are low in orientation but also have little free-fall duration based on checking duration and how close the magnitude of acceleration the signal is to zero during free fall (little free-fall is defined by a short duration of time spent in free-fall just prior to the faller making impact with the ground). Using these criteria, orientation change, free-fall, and peak-magnitude thresholds are calculated from empirical data sets to produce this characteristic segmentation of fall signatures defined by steps 458-466. Physically, this characteristic segmentation a faller that may not be completely horizontal when falling from a vertical position and slowly fall to the ground.

If none of the conditions are met from steps 408-466, the method progresses to step 470 where the increment (i) is updated to extract the next value in the magnitude buffer. In Step 472, (i) is checked to see if it equals the length of the buffer (i.e., all data in the buffer has been analyzed). This would indicate that the just-monitored data set did not result from a fall and method 400 progresses to block 474, where control returns to method 300 to start the process of monitoring data to detect a high acceleration magnitude again.

At step 472, if the increment (i) is not at the end of the filtered magnitude buffer then the method returns to step 406 where the next filtered magnitude value is extracted from the magnitude buffer to be checked in steps 408, 418, 428, 438, 448, and 458. The order of the 408 through 466 comparisons and mathematical operations are preferably chosen to decrease the processing time in evaluating a potential fall, such that on the method first checks for simpler, more common features and characteristics in the signal. The structure of classification categories changes based on prevalence of fall events in the training set of data. This approach generates a better way of detecting fall and generates better results versus using traditional techniques such as neural networks, pattern recognition, or other classical machine learning methods because fall signature sets are never an exact representation of all the falls that can occur.

Furthermore, in each category, each sample of the buffer is analyzed for: different sized magnitude spikes (threshold value MFt), changes in orientations (threshold value ORt), different sized buffers of data having a number of samples with magnitude data (findZeroGvec based off ZGt that determines the size of the vector) falling below different threshold values (ZGt), and ensuring that a number of samples falling below the ZGt threshold value does not exceed a certain number (SuZGt). Shown are six types of categories that correspond to different types of falls that occur. Listed below each stage in FIG. 4, in the chart, is the type of fall that the stage is evaluating. The threshold values for each stage are made by evaluating data sets of falls and processing them to group them in these six categories based on the features defined with the stage. If one of the six stages is considered to be a fall then the processor outputs a signal that indicates that a fall has occurred as indicated in steps 416, 426, 436, 446, 456, and 466. More than six stages can be used to further refine different fall types. In addition, a data set acquired during real, in-situ, use can modify the various thresholds for a given category after the method has classified the data set as a fall according to the steps in FIG. 4 corresponding to the given category. Thus, reference herein to empirical data sets can refer to in-situ data sets (e.g., data resulting from an intended end-user that falls).

Different Classifications of Falls by Means of Pressure Readings

Fall detection devices use accelerometers and/or gyroscopes to provide indication based off a change of orientation, a large acceleration magnitude spike correspond to a large impact, elements i.e., acceleration magnitude and duration) of free-fall before the large impact, and the shape of the accelerometer magnitude signal. The signal that is collected and analyzed is often triggered by either elements of free-fall, rate of change of pressure from sensors, or a large magnitude of acceleration from hitting the ground during a fall. Any of these defined triggers can be used as a full trigger to further refine based off the data and if a device should output a signal indicating a fall or non-fall event has occurred.

In addition to accelerometers, a fall detection device may also use a pressure sensor that produces an output proportional to the barometric pressure surrounding the device. A pressure delta value is the difference between the barometric pressure before a fall trigger and the barometric pressure after a fall trigger. A processor in the fall detection device can refine the determination (that was based just on acceleration magnitude) that a fall has occurred by comparing a measured and calculated pressure delta value with an associated pressure delta threshold value. Thus, the processor may compare the determined pressure threshold value, in addition to a comparison of a value from an acceleration, measuring device to an associated fall trigger threshold, and determine that one of a plurality of fall types occurred based on the magnitude of the pressure delta value.

Different falls correspond to different changes of orientation, different large impacts, different elements of free-fall before the large impact, and different shapes of the magnitude accelerometer signals. These different components are processed separately to provide a clear indication of what type of fall occurred. One such example is the difference between a fall where the person, or object, spins while falling and lands on their side on soft ground versus a forward fall with a large impact on hard ground. Characteristics that distinguish the two potential fall categories might include a large orientation change but little free-fall and for magnitude impact as corresponding to a first category and characteristics that distinguish events of a second category from the first might include having a small orientation change, a large amount of free-fall and a large magnitude impact. Accordingly, it is beneficial to process these two different types of falls with different sets of parameters. The different categories of falls in method 400 provide examples of different types falls flat are determined based on monitored acceleration values.

To better indicate when a fall occurs a pressure sensor is used to sense the relative altitude (shown in FIG. 5 with method 500) in additions to the further means to classify, or characterize, data from a potential fall event. Method 500 defines how pressure and a combination of accelerometers and/or gyroscopes can be used to detect a fall based on classifying the fall in one of many categories. The method starts at 510 and progresses to 520 where accelerometer, gyroscope, a combination of both, and pressure data is sampled. When data from a device's measurement sensor means indicates a trigger that may correspond to a fall event, (e.g., one or more accelerometers indicating a free-fall occurrence or a large magnitude spike, one or more barometers outputting data used to determine pressure rate of change, one or more gyroscopes indicating orientation change, or a combination data from these, or other, sensors for detecting physical aspects of the device's environment), the average pressure before the trigger is compared to the average pressure after the trigger to indicate that a person using the device has changed orientation and is lower in altitude. Shown in step 530, using the pressure data collected, a pressure change is calculated from pressure data before and after the trigger. Using the pressure difference calculated in step 530, steps 540 and 550 compare the pressure change to a first pressure threshold and to a second pressure threshold to classify whether the pressure change is greater than one of the pressure thresholds. If the pressure change is greater than the first pressure threshold (i.e., the determined pressure change experienced by the device satisfies the first threshold criteria), the method progresses to step 560 where further refinements can be made to better indicate if the method sense a fall. The first pressure change threshold/criterion is determined from analyzing empirical fall data sets that are subsets of a larger data set of collected pressure data from collected data known to represent fall events. Otherwise, step 540 progresses to step 550 where the pressure change is compared to second pressure threshold/criterion that is generated by typical pressure changes for a plurality of frills not contained in the data set, or sets, used to determine the first pressure change threshold.

In step 560, the processor in the device performs further processing to characterize potential fall events that correspond to the first pressure threshold to better determine whether to indicate a fall within a characteristic, segmentation of falls. Furthermore, in step 570 further refinements can be done based on fall events in the empirical data set that the second pressure threshold is determined from that defines a different characteristic segmentation of falls. The further refinements can be based on the gyroscope, accelerometer and pressure data collected based on the trigger defined in step 530. Once performing further characterizations in step 570 or 560, the method progresses to step 580 where the method outputs a signal to indicate that a potential fall event data under evaluation is indeed a fall event.

Figure 5:
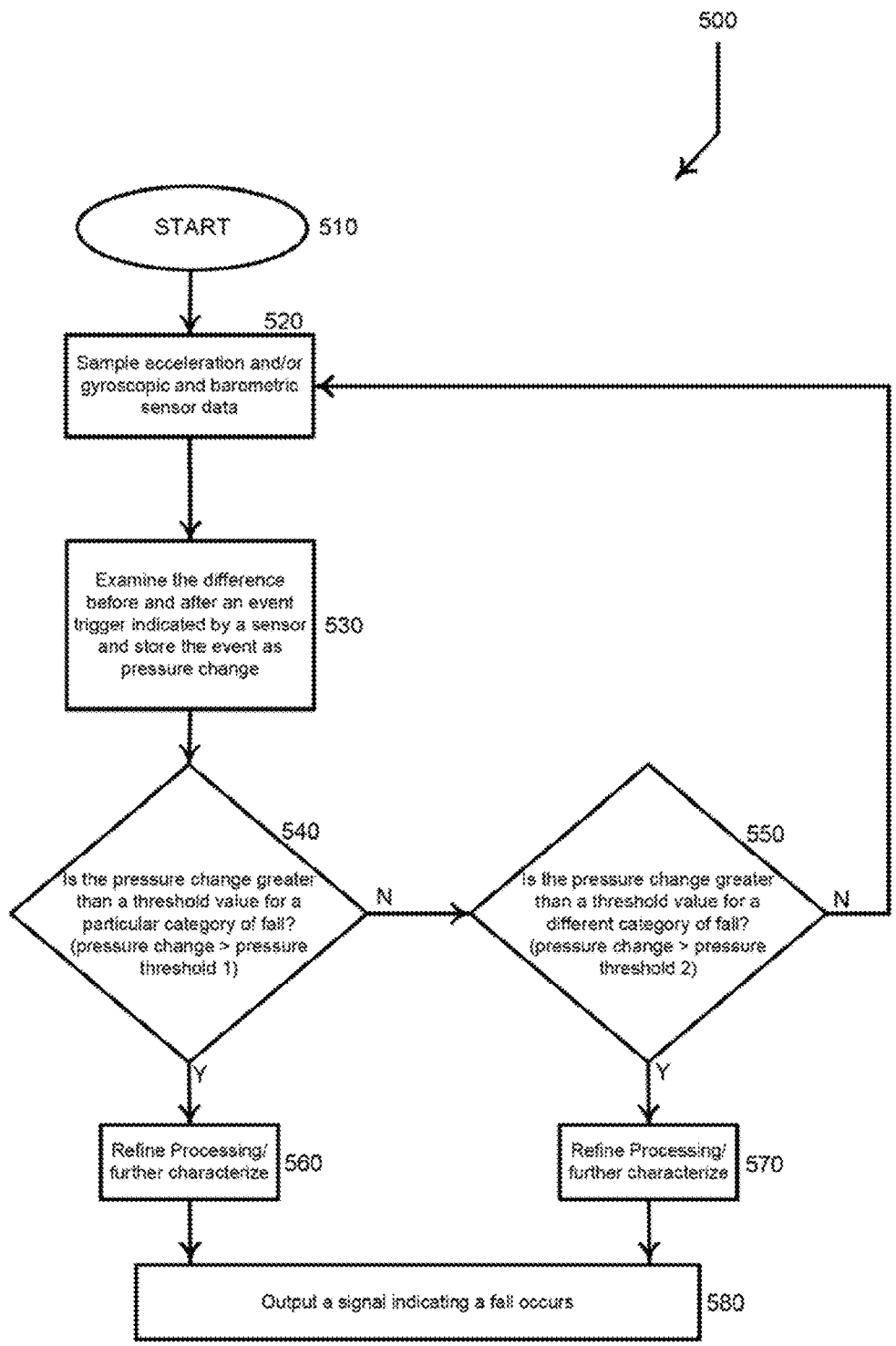
FIG. 5 illustrates a flow diagram of a method for indicating that a fall occurs by classifying multiple changes in pressures based on different types of falls.

To better classify falls, different pressure delta threshold values (and other parameters corresponding to the characteristics of different fall data segmentations) are used because a fall from a chair has a different change of orientation, a different large impact spike, different elements of free-fall before the large impact, and different shapes of the magnitude accelerometer signals along with different changes in pressure when compared with data of a fall of a person standing upright. FIG. 5 shows characterizing potential fall event data where pressure change from before a trigger to after a trigger event differs depending on a fall type. The threshold values are different for different falls to better distinguish between falls and false-positives. If either set of conditions is met then the processor outputs a signal that indicates that a fall occurred.

More than two pressure threshold comparisons may be used to further refine the evaluation of potential fall event data, wherein more than two pressure thresholds correspond to more than two respective categories having respective characteristics, or characteristic segmentations of fall data sets. Such characteristic segmentation could, for example, correspond to the six columns of analysis discussed above in reference to FIG. 4. It will be appreciated that only two characteristic segmentations have been used for simplicity of discussion and illustration in the figures, but the claims may recite more than just a first and second thresholds for magnitude, orientation, pressure, sound, light, and other measurable parameter.

Figure 6:
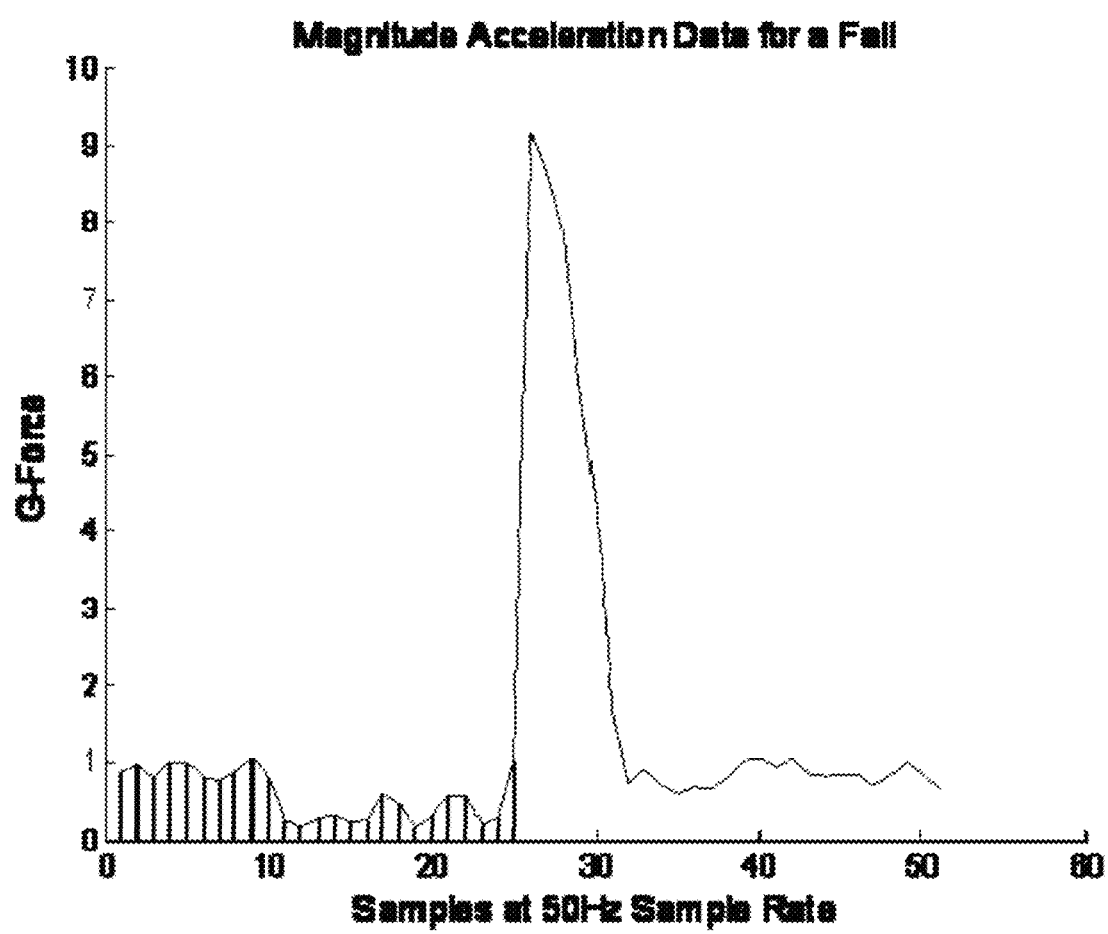
FIG. 6 illustrates a magnitude plot from a fall detection device during a fall event.
Figure 7:
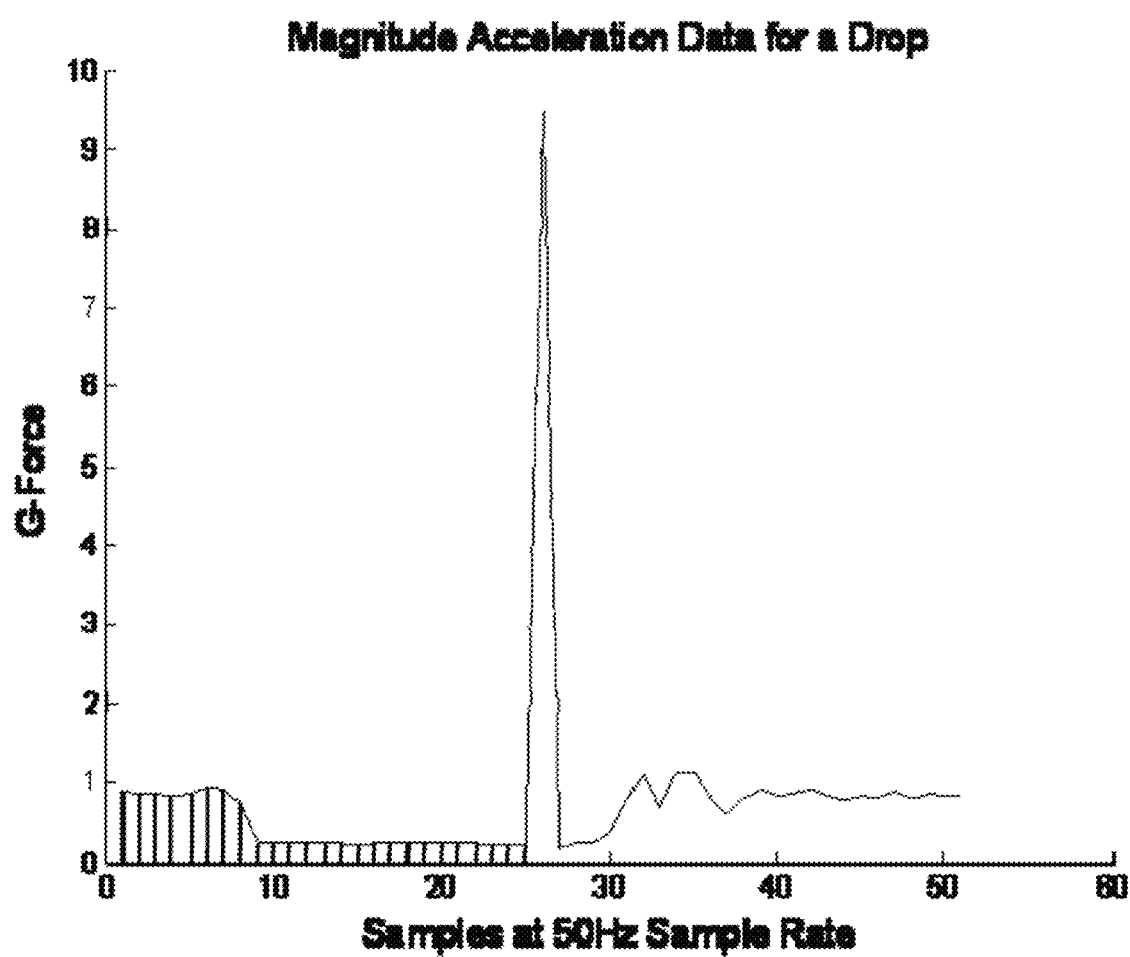
FIG. 7 illustrates a magnitude plot from a fall detection device during a drop event.

Using an Integration Technique to Determine the Difference Between False Positives and Falls in Fall Detection Devices When humans fall down, accelerometer signals register a period of free-fall prior to a large impact found in the magnitude of acceleration. Furthermore, this free-fall lasts a shorter period of time for typical drops than for typical falls. FIG. 6 shows the magnitude plot of a 3-axis accelerometer for a typical fall. Also, FIG. 7 shows the magnitude plot for a typical drop. To decipher the difference between a drop and a fall in a fall detection device, an indication (trigger) that a fall may have occurred is given by a large magnitude spike of acceleration. Alternatively, a period of the magnitude signal close to zero G-force typically corresponds to the start of a potential fall.

Figure 8:
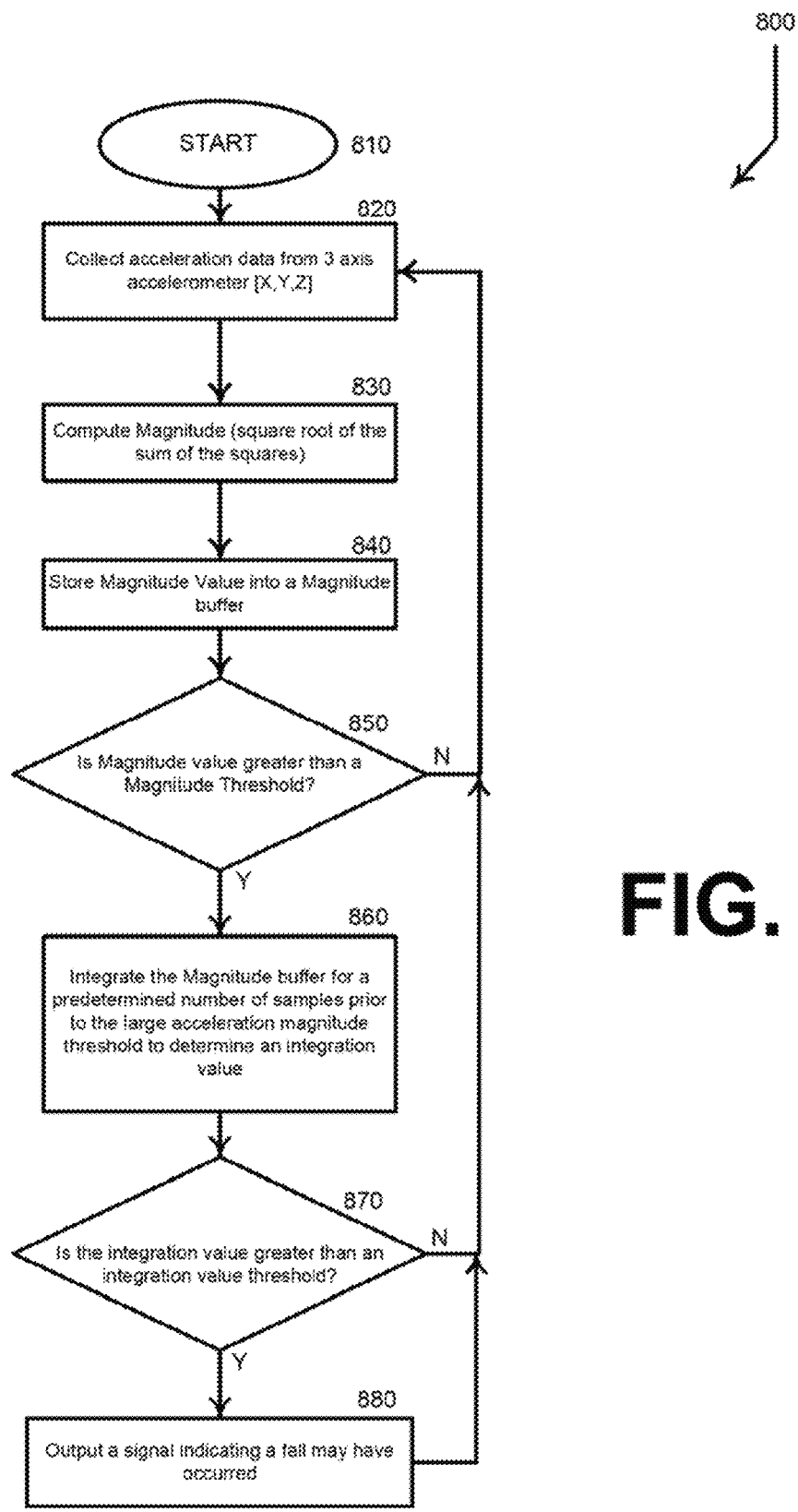
FIG. 8 illustrates a flow diagram of a method to output a fall signal based on an initial threshold and integration of the period of free-fall prior to an impact of a potential fall.

FIG. 8 illustrates method 800 for determining the difference between a drop and a fall. The method in FIG. 8 starts at step 810 and progresses to step 820 to sample acceleration data then calculates the acceleration magnitude for each (X,Y, Z) axis accelerometer signal and stores the magnitude value into a data buffer that facilitates recalling a historic representation of the magnitude signal as shown in steps 830 and 840. After that, each magnitude value sampled from the accelerometer is then compared to a threshold value that is empirically determined from collected magnitude data for typical falls in step 850. In step 860 with a large acceleration magnitude sensed, the historical magnitude data is recalled and integrated over predetermined period referenced to, and prior to, the large magnitude. The integration of the magnitude signal over predetermined period shown in FIGS. 6 and 7 is indicated by the vertical shading prior to the larger acceleration spike. In step 870 the integration value determined from this chosen region is then compared to an empirically determined value. The empirical value is preferably determined from a minimum value obtained from a set of fall signatures. An integration value corresponding to the region preceding the large magnitude value that is less than the empirically determined integration threshold value indicates a non-fall because a free fall typically has an acceleration magnitude signature close to zero, thus the integral of the magnitude signal preceding the spike will be much lower than that of the similar preceding area of a fall event, if not zero. If the value is greater than the threshold value then the method outputs a signal indicating that a fall has occurred as shown in step 880.

Figure 9:
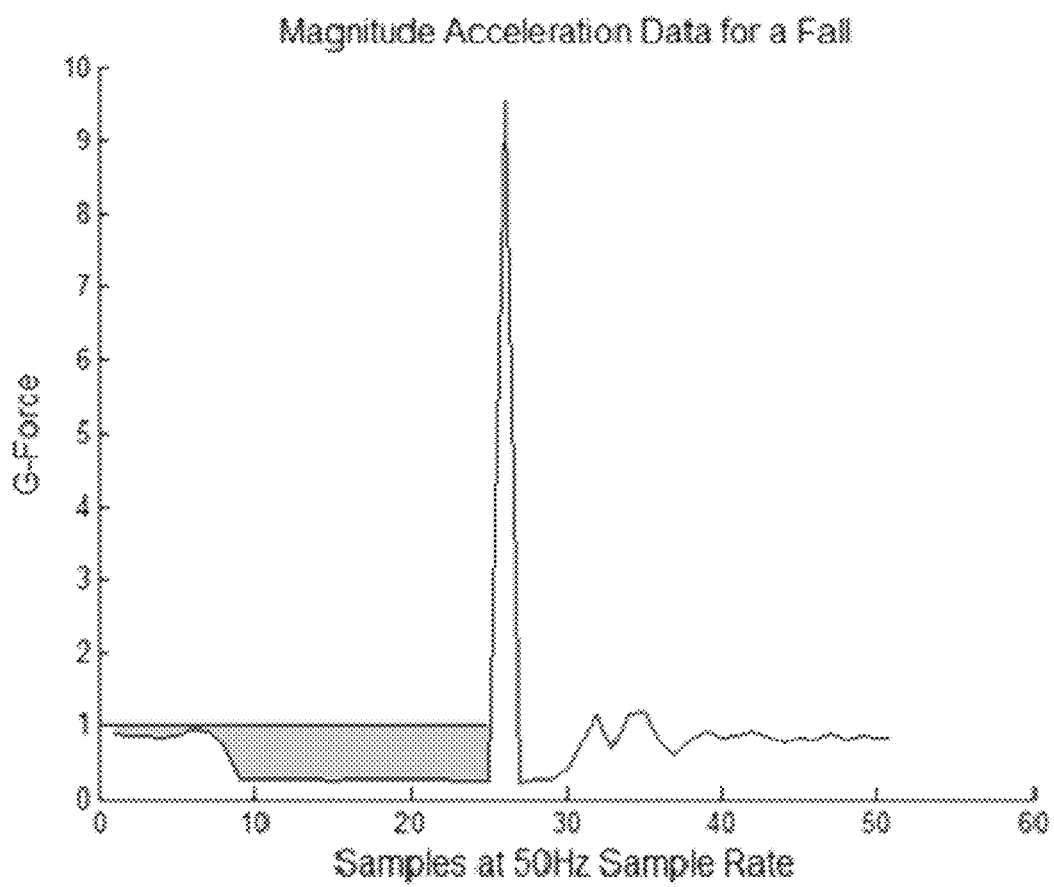
FIG. 9 illustrates a plot showing an integration region for an embodiment of a method for sorting the difference between drops and falls.

An alternative to integrating to determine the area below an entire curve is to integrate values between the occurrence of reaching a predefined acceleration limit and actual acceleration values from the signal to eliminate large acceleration spikes before the fall attributing to the area given by the integration value which is the area found between one or a defined threshold value and the magnitude signal. The integration value would then be compared to a threshold value to see if it is less than the threshold value. Shown in FIG. 9 is a typical fall and the new area of integration indicated by the shaded region.

Fall Detection Wrist Worn Device that Recognizes Attachment to Wrist

Figure 10:
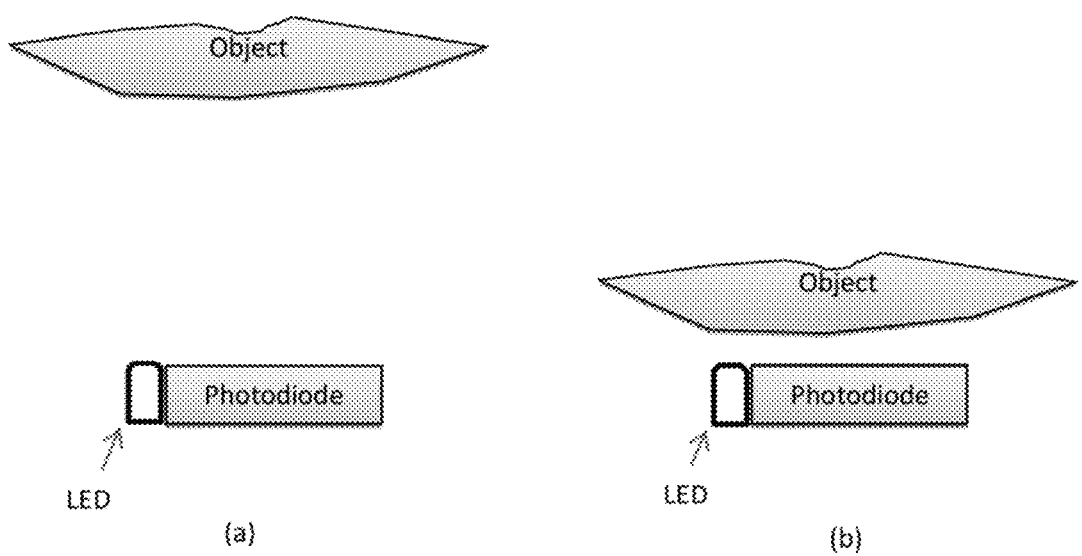
FIG. 10 illustrates a demonstration of use of a proximity sensor in a fall detection device.

Wrist worn fall detection devices are prone to indicating non-fall events as fall events when detached from the wrist and are easily susceptible to classifying typical drops, or other events, improperly as falls. A proximity sensor typically comprises a photodiode and an Infrared LED that produces an output corresponding to changes in the infrared light from the LED. This is illustrated in FIG. 10 by showing the basic setup of a proximity sensor. When the object is away from the sensor (a) light emitted and picked up from the photodiode is not as intense as when the object is close to the led and photodiode (b). Thus, it can be sensed that the object is close to the proximity sensor.

Figure 11:
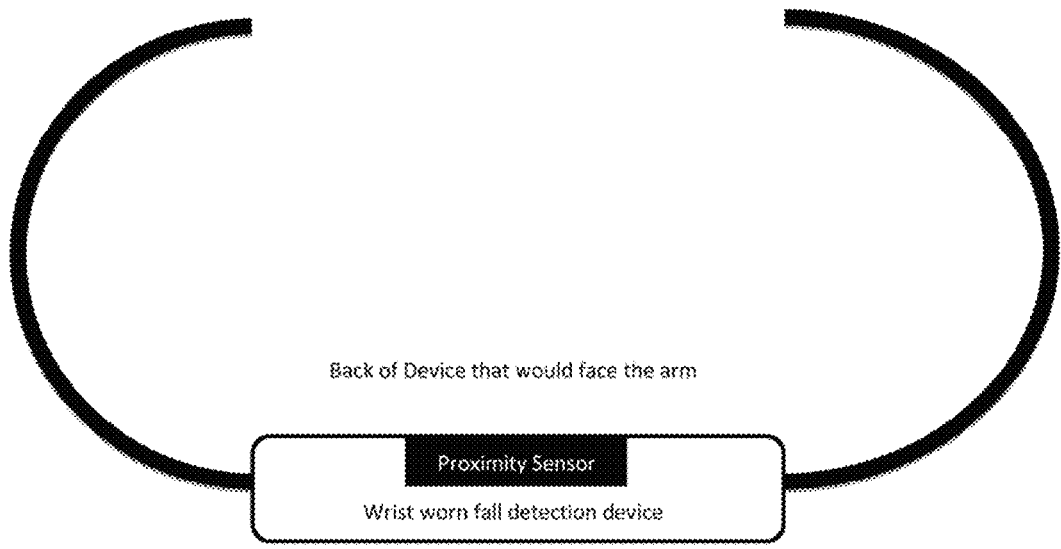
FIG. 11 illustrates use of a proximity sensor in a wrist worn device to activate a fall detection algorithm.
Figure 11:
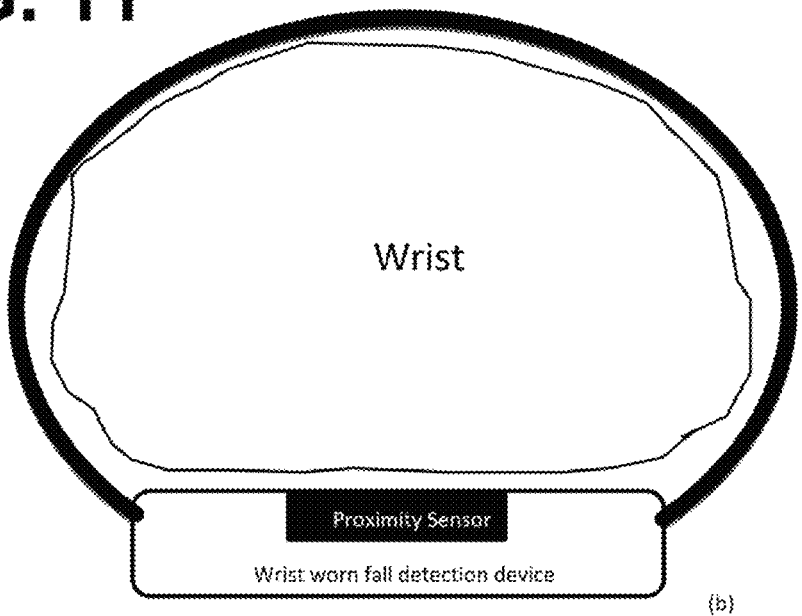

In a wrist worn fall detection device, the proximity sensor is placed on the back of the device so as to sense when the device is attached to the arm. FIG. 11 illustrates a typical way that the sensor is oriented to detect if the device is on the wrist. FIG. 11(*a*) shows the fall detection device when it is not attached to the wrist. Once attached to the wrist (*b*) the light level sensed by the photodiode from the LED is reduced thus producing a signal that indicates that a full detection algorithm and devices, including an accelerometer, barometer, and/or and a gyroscope contained in the fall detection device should be activated, or enabled, to sense if a person has fallen down. This reduces the occurrence of non-fall events being classified as fall events and reduces power consumption because the fall detection sensors are in a low power, or sleep state while the proximity device of a fall detection device indicates that the fall detection device is not on a person, animal, or object.

Figure 12:
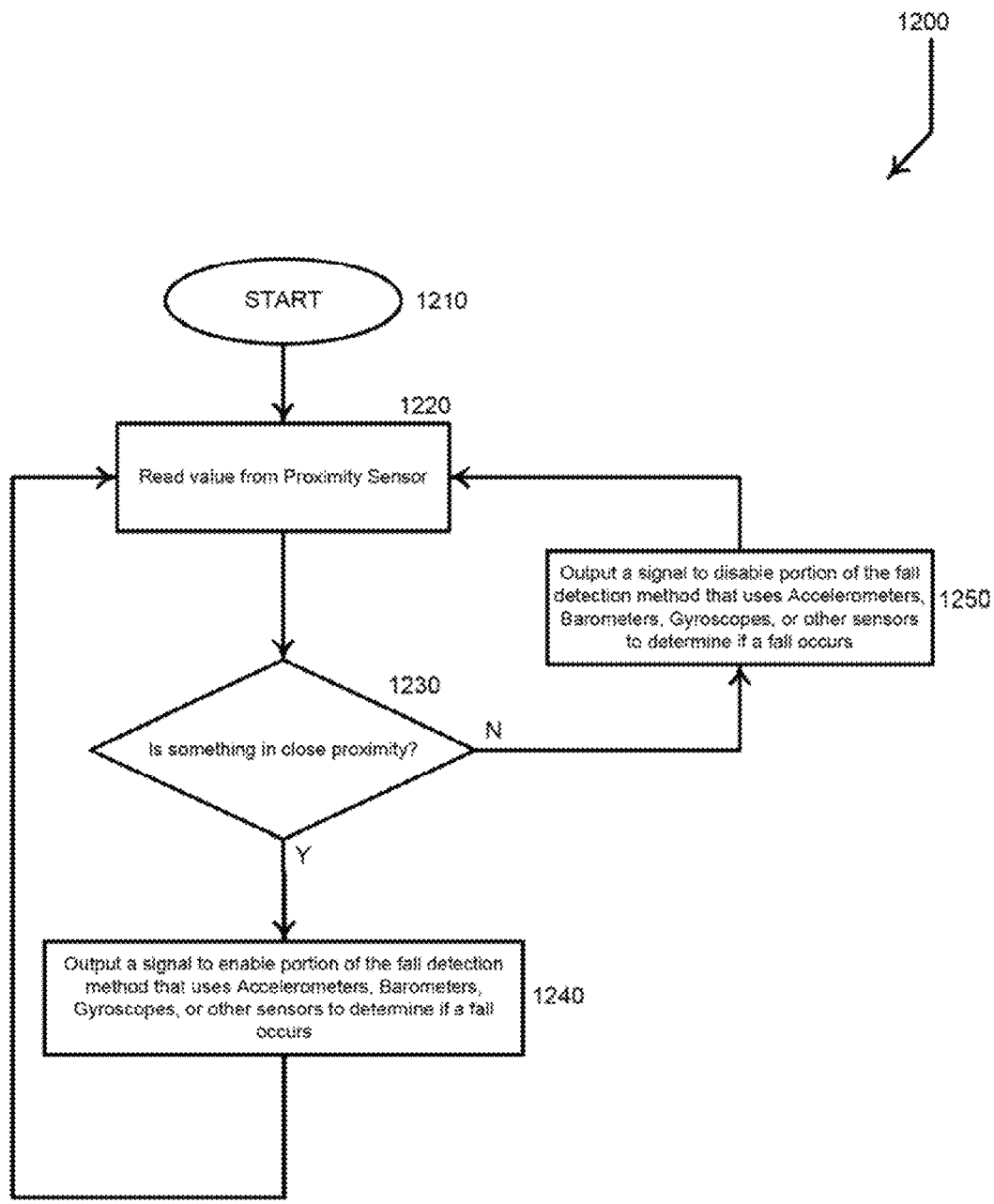
FIG. 12 illustrates a flow diagram of a method to output a signal when a fall detection device is attached to a person's wrist to enable the device to start sensing for falls.

The method to determine if a fall has occurred while using a proximity sensor to define when to enable a fall detection method is shown in method 1200 as a flowchart in FIG. 12. Method 1200 starts at step 1210 that progresses to step 1220 which reads values from the proximity sensor. For the purposes of this method it is assumed that the proximity sensor outputs a logical value that tells if an object is close or not. However, there are many ways for a proximity sensor to output data and include voltage values that indicate if an object is near, the sensors could output the closeness it believes that an object is and specify of its measurements and all of these factors could describe how close an object is to the proximity sensor. Shown in step 1230, if an object is sensed to be close to the proximity sensor then it is assumed that the device is on the wrist so a signal is output to activate sensors and a method based on sensors activated to determine if a fall has occurred as indicated in step 1240 and then progresses back to step 1220 to determine if the all detection method should be disabled when an object is no longer sensed by the proximity sensor. If an object is sensed as not close to the proximity sensor then method follows the 'Y' path from step 1230 and disables the fall detection method and returns to reading values from the proximity sensor to enable the fall detection method when something is sensed to be in close proximity. Typically, the proximity sensor is operated to check for proximity to an object at a rate of 1-2 times per second but may be chosen be faster or slower depending on power, or other, constraints of the fall detection device.

This device is not limited to being attached to only a person's wrist. The device could be used to sense if a fall detection device is attached any portion of a body. For example, fall detection devices could be attached to different parts of the arms or legs. Likewise, this approach can be used sensors containing a proximity sensor that attach to any area of the body like an adhesive bandage to sense if the sensor is close to the skin and also contain other sensors like accelerometers to sense impact, acceleration orientation change, or free-fall of a person to indicate a fall.

Figure 13:
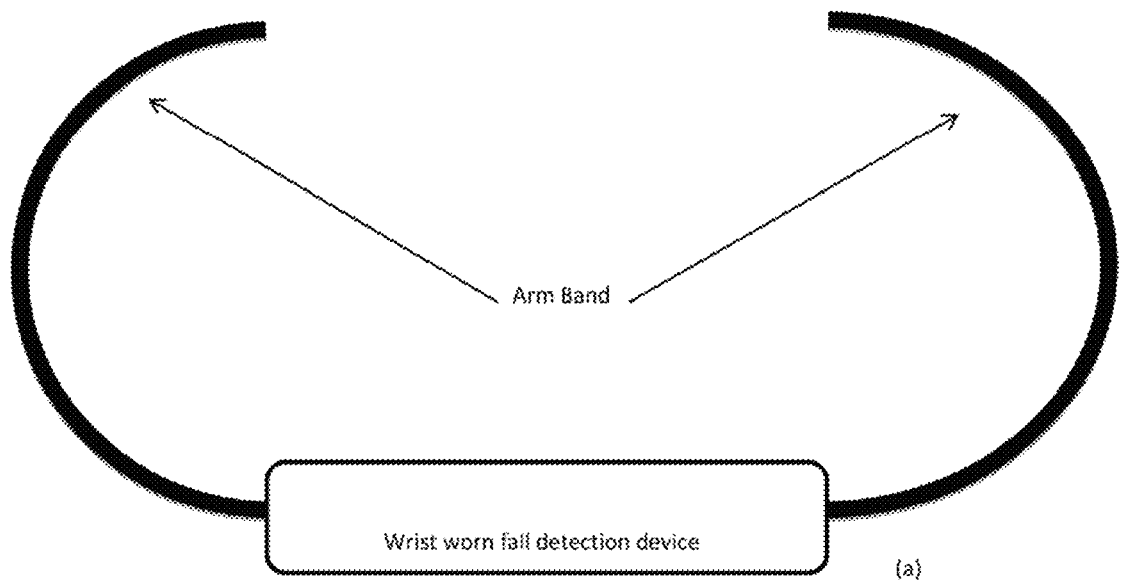
FIG. 13 illustrates use of a closed circuit arm band in a wrist worn fall detection device to activate a fall detection algorithm.
Figure 13:
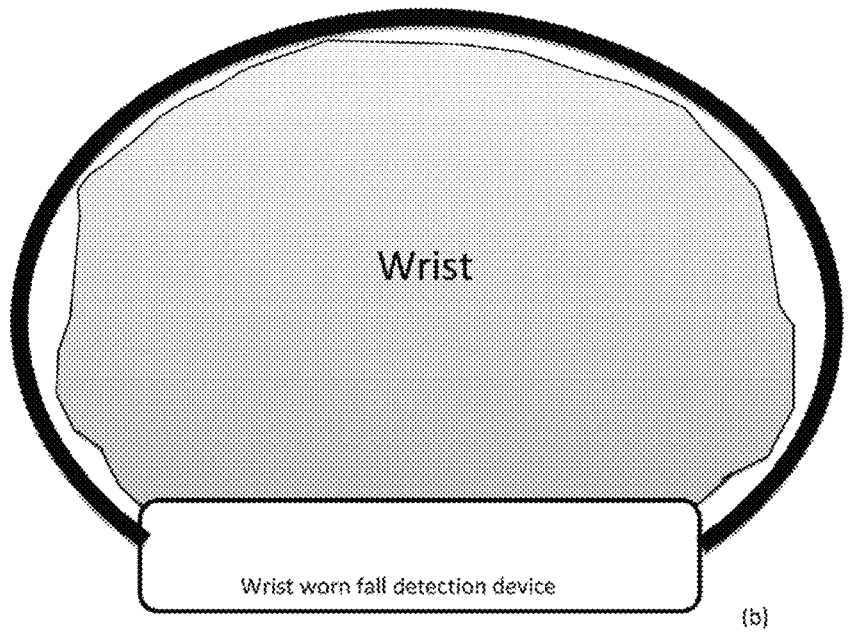

Closed Circuit Band Indication of Attachment for a Fall Detection Device to Human Limb Fall detection devices that attach to the arms, or legs are fastened by a band to retain the device on the person. In this fall detection system, the band contains a metallic coating or wire within that completes a dosed circuit when the band is attached. Illustrated in FIG. 13 (*a*), is the fall detection device with the arm band not attached creating an open circuit. If the band is attached, a closed circuit is created (FIG. 13(*b*)). An electrical signal flows though the closed circuit indicating that each side of the wrist band is attached. If the voltage is zero volts or current is zero amps, the device operate as if not attached to a limb and the fall detection device will not rely on other sensors to determine if a fall has occurred. If a voltage or current is being introduced to the closed circuit within an arm band remains the same from one side to the other then fall detection sensors can be used and a fall detection method, and system of sensors and other components can be enabled to detect falls.

Likewise, the impedance of the armband can be checked to determine whether the device is attached or not attached to the limb. If the resistance on the band is infinite then the band does not complete a circuit. If the resistance on the band is zero, or close to zero, then the band completes a circuit. If a resistance of zero, or close to zero, is detected then fall detection sensors and a method for processing signals from the sensors may be enabled to detect falls.

Figure 14:
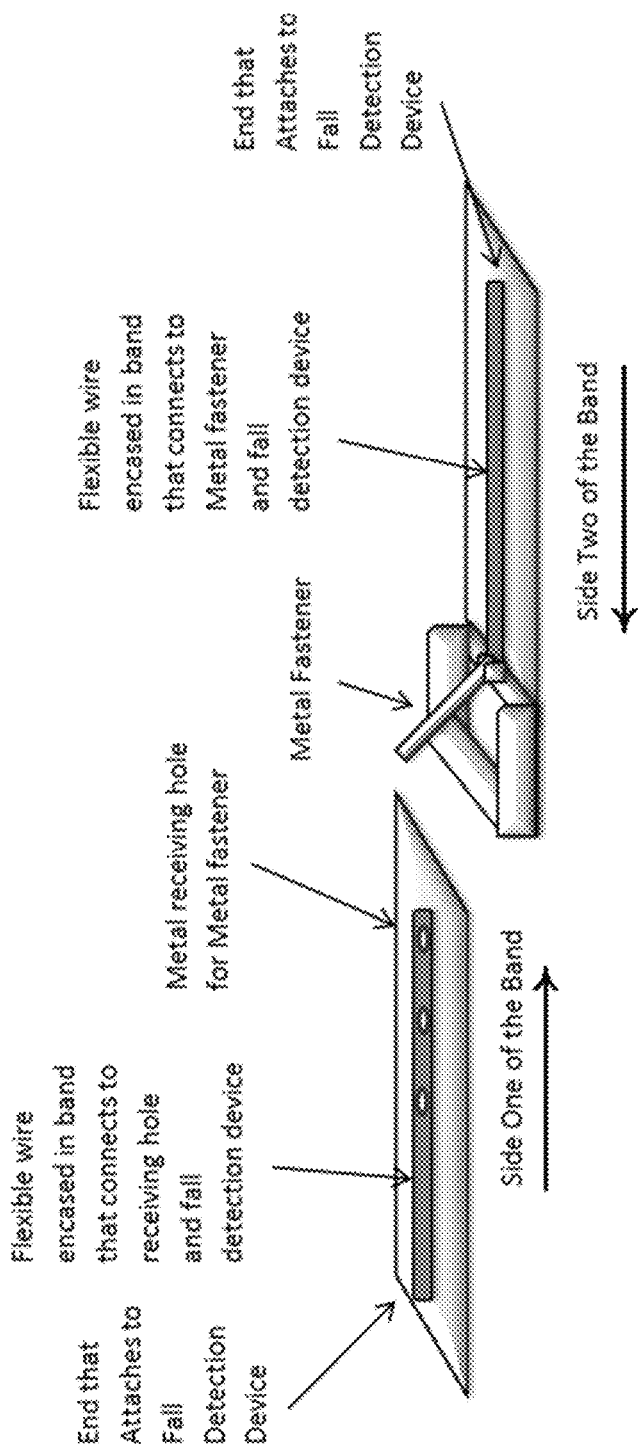
FIG. 14 illustrates a closed circuit securing band with a metallic fastener.
Figure 15:
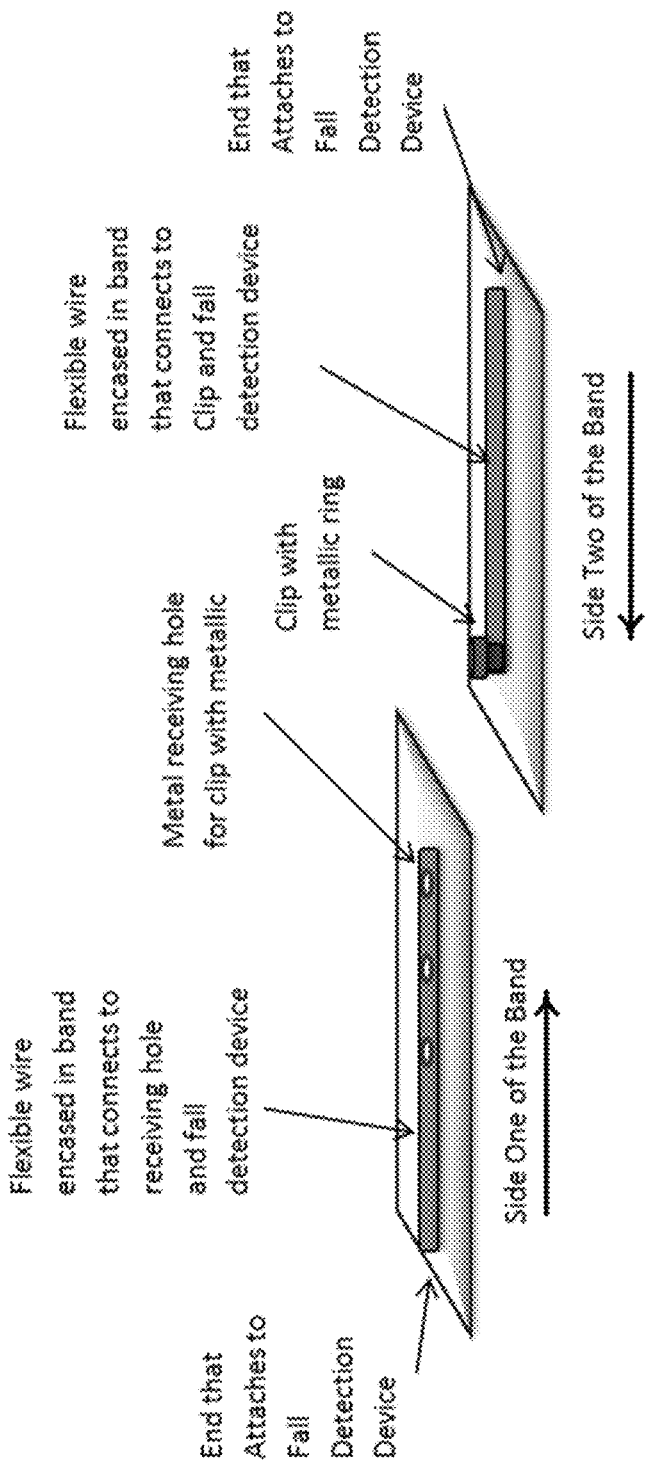
FIG. 15 illustrates a closed circuit securing band with a metallic clip fastener.

FIGS. 14 and 15 show two possibilities for physical connections for the band that secures a fall detection device to a person, animal, or object. FIG. 14 shows a metal fastener with an included wire encased in the band in order for an electrical, signal to flow to complete a closed circuit when attached. The receiving holes for metal fastener contain a metallic coating in order to make a connection between the two bands. Likewise, FIG. 15 shows a push-in clip that forms an electrical connection so that a complete circuit is formed when the two ends are connected. The wires shown as shaded regions are encased in the band as to not make connections with anything other than the fastener. These two connection varieties are used for the closed circuit connection discussed above that enables fall detection sensors and a method for processing signals from the sensors.

Proximity Sensor Contained in Band to Detect when Device is Attached

Figure 16:
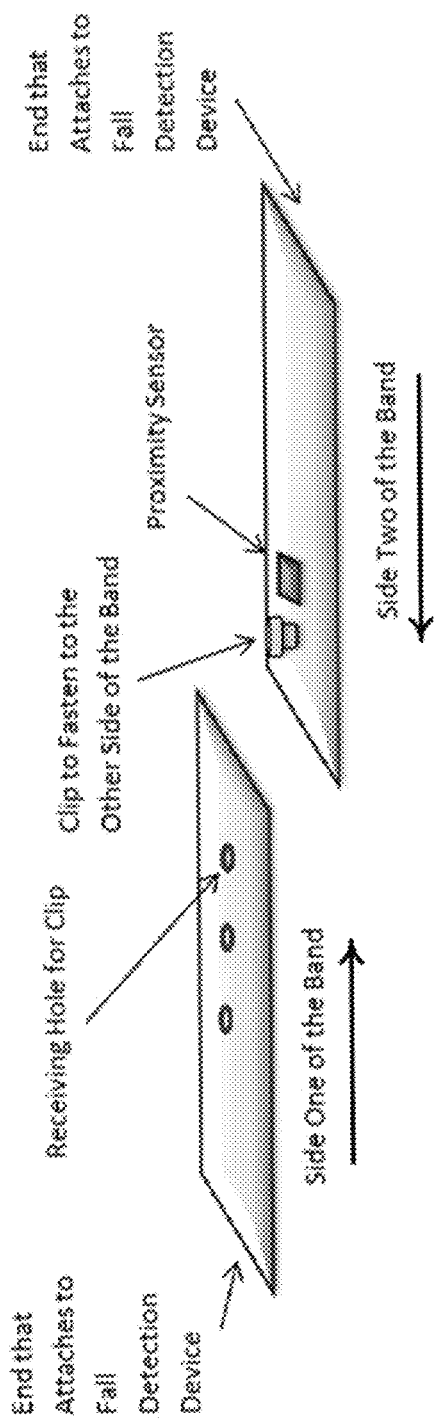
FIG. 16 illustrates use of a proximity sensor connected to a band in fall detection device to activate a fall detection method.

FIG. 16 shows the two sides of a band of a fall detection device's limb band. The figure shows receiving holes that allow a clip to fasten within the holes from the other side of the band so that the band can be attached to a portion of the body. In order to ensure that the device is fasten to a portion of a person when the fall detection device determines that a fall may have occurred, an optical proximity sensor within the band outputs a signal indicating that the band is within close proximity to a second region of the band when the clip is connected. By determining that the two sides of the band are fastened based on the proximity sensor outputting a signal that the sensor remains in close proximity to an object for a sustained period of time, sensors and a method can be enabled within a fall detection device to start checking if a fall occurs. This reduces false positives within a fall detection method by knowing that the device is attached to the body and reduce power consumption by enabling sensors such as barometers, accelerometers, and gyroscopes only when the device is attached to the body.

Smartphone Application

In another aspect, an application running on a smartphone, or other mobile device, can use the methods disclosed herein. Presently, smartphones typically include only one three-axis accelerometer device. However, as more and more mobile devices include redundant sensors, such as accelerometers, barometers, gyroscopes, magnetic field sensors, electric field sensors, microphones, light sensors, cameras, and the like, differential analysis of signals generated by the redundant sensors, which may be positioned in the smartphone, or other mobile device, at opposing, corners, edges, surfaces, locations, etc., to maximize distance between each redundant sensor, can provide information used by the mobile device to determine its orientation with respect to an individual carrying, wearing, or otherwise possessing, the device on his, or her, person. Having determined the orientation of the device with respect to a person, then the methods disclosed herein, and running on the mobile device can accurately determine that the person has fallen.

It will also be appreciated that the methods, systems, and devices disclosed and claimed herein may be used in application other than detecting that a wearer has fallen. For example, data sets from known vehicle crash events may be categorized according to similarity of event data signatures, and could thus be used to generate multiple criteria corresponding to multiple respective crash event data set categories. Such use could reduce reporting non-crash events to a telematics services provider, or emergency services provider, an indication that a vehicle crashed when in fact it did not. Other uses could include detecting the striking of a door to a dwelling and determining whether a strike was the knocking down/open of the door by a potential intruder or just a visitor knocking on the door. In such a scenario, instead of analyzing characteristics of a period of free-fall before an impact of a potential strike event, the position of the door (open, closed, or in between as detected by a door position sensor) could reduce the reporting of a break-in following a large acceleration event (striking of the door), if the door remains closed.

The invention claimed is:

1. A device for characterizing potential fall event data, comprising:
    a processor configured for:
    loading a first acceleration magnitude threshold value from a memory;
    loading a second acceleration magnitude threshold value from a memory;
    sampling acceleration data received from an acceleration measuring means of the device;
    storing the sampled acceleration data into a memory capable of storing a predetermined number of sampled acceleration data samples;
    determining a calculated magnitude acceleration value from the acceleration data for each sample;
    comparing the calculated magnitude acceleration value to the first acceleration magnitude threshold value for each sample;
    comparing the calculated magnitude acceleration value to the second acceleration magnitude threshold value if the calculated magnitude acceleration value does not exceed the first acceleration magnitude threshold value, wherein the first acceleration magnitude threshold value corresponds to a first characteristic segmentation of fall event data sets and the second acceleration magnitude threshold value corresponds to a second characteristic segmentation of fall event data sets; and
    outputting a signal indicating that a fall may have occurred if the calculated magnitude exceeds either the first or the second acceleration magnitude threshold values.

2. The device of claim 1 further comprising performing further analysis of the stored sampled acceleration data if the calculated magnitude acceleration value exceeds the second acceleration magnitude threshold value.

3. The device of claim 2 wherein the further analysis includes:
    sampling, orientation information from an orientation measuring means of the device;
    determining a change in orientation of the device between a time corresponding to a sample where the calculated magnitude acceleration value exceeded either of the first or the second acceleration magnitude threshold values and a time corresponding to a sample that precedes the sample where the calculated magnitude acceleration value exceeded either of the first or the second acceleration magnitude threshold values by the predetermined number of samples;

outputting a signal indicating that a fall may have occurred if the determined change in the orientation of the device exceeds a predetermined orientation threshold; and wherein the predetermined orientation threshold corresponds to one of the first or second acceleration magnitude threshold value, and wherein the predetermined orientation threshold has a different value if it corresponds to the first acceleration magnitude threshold value than if it corresponds to the second acceleration magnitude threshold value.

4. The device of claim 1 wherein the processor is further configured for:

sampling orientation information from an orientation measuring means of the device;

determining a change in orientation of the device between a time corresponding to a sample where the calculated magnitude acceleration value exceeded either of the first or the second acceleration magnitude threshold values and a time corresponding to a sample that precedes the sample where the calculated magnitude acceleration value exceeded either of the first or the second acceleration magnitude threshold values by the predetermined number of samples;

outputting a signal indicating that a fall may have occurred if the determined change in the orientation of the device exceeds a predetermined orientation threshold; and wherein the predetermined orientation threshold corresponds to one of the first or second acceleration magnitude threshold values, and wherein the predetermined orientation threshold has the same value regardless of whether it corresponds to the first acceleration threshold value or to the second acceleration magnitude threshold value if the first acceleration magnitude threshold value and the second acceleration magnitude threshold value are substantially the same.

5. The device of claim 1 wherein each sampled acceleration data includes acceleration magnitudes for three axes, and wherein the processor determines for each sample the calculated magnitude acceleration value by calculating a square root of a sum of squares of the acceleration magnitudes for the three axes.

6. The device of claim 1 wherein each calculated magnitude acceleration value is processed with a filter into a filtered calculated magnitude acceleration value before comparing to either of the first and second acceleration magnitude threshold values.

7. The device of claim 2 wherein the further analysis includes comparison of at least one of an integral, a mean, a median, an average, a standard deviation, and Fourier analysis result to corresponding integral, mean, median, average, standard deviation, or Fourier analysis result values for characteristic segmentation.

8. A device for characterizing potential fall event data, comprising:

a processor configured for:

loading a first acceleration magnitude threshold value and a gravitational proxy value from a memory;

sampling acceleration information from an acceleration measuring means of the device at a predetermined sample rate into sampled acceleration data;

determining a calculated magnitude acceleration value from the sampled acceleration data for each sample;

storing the calculated magnitude acceleration values into a memory capable of storing a predetermined number of calculated magnitude acceleration values corresponding to a predetermined number of samples of acceleration data;

comparing each calculated magnitude acceleration value to the first acceleration magnitude threshold value;

evaluating the predetermined number of calculated magnitude acceleration values to determine a number of samples composing a fall evaluation period, wherein a calculated magnitude acceleration value that drops below the gravitational proxy value indicates a beginning of the fall evaluation period, and wherein the predetermined number of calculated magnitude acceleration values corresponds to samples during the fall evaluation period occurring before a sample having a calculated magnitude acceleration value that exceeds the first acceleration magnitude threshold value;

comparing the number of samples in the fall evaluation period to a fall evaluation period limit value, wherein the fall evaluation period limit value is determined from empirical fall data; and outputting a signal indicating that a fall may have occurred if the number of samples in the fall evaluation period does not exceed the fall evaluation period limit value.

9. The device of claim 8, wherein the predetermined fall evaluation period limit value is a predetermined amount of time.

10. The device of claim 8 wherein the predetermined fall evaluation period limit value is a predetermined number of samples.

11. The device of claim 8 wherein the predetermined fall evaluation period limit value corresponds to an empirically determined period of free-fall for fall event data sets in a characteristic segmentation that corresponds to the first acceleration magnitude threshold value.

12. The device of claim 8 wherein each calculated magnitude acceleration value is processed with a filter into a filtered calculated magnitude acceleration value before comparing to the first acceleration magnitude threshold value.

13. A device for characterizing potential fall event data, comprising:

a processor configured for:

loading a first elevation change threshold value from a memory;

loading a second elevation change threshold value from a memory;

determining that data from one, or more, measurement sensor means, corresponding to one, or more, respective parameters, indicates that a trigger event has occurred;

evaluating data generated, by at least one of the measurement sensor means that measures pressure, before the trigger event with data generated after the trigger event to result in an elevation chance value;

comparing the elevation change value with the first elevation change threshold value;

comparing data from one, or more, of the measurement sensor means to first criteria for the one, or more, corresponding parameters if the elevation change value exceeds the first elevation change threshold value, wherein the first criteria corresponds to the first elevation change threshold value;

characterizing the potential fall event data as a fall event if the data from the one, or more, measurement sensor means satisfies the first criteria;

if the data from the one, or more, measurement sensor means does not satisfy the first criteria, comparing data from one, or more, of the measurement sensor means to second criteria for the one, or more, corresponding parameters if the elevation change value exceeds the second elevation change threshold value, wherein the second criteria corresponds to the second elevation change threshold value; and characterizing the potential fall event data as a fall event if the data from the one, or more, measurement sensor means satisfies the second criteria.

14. The device of claim 13 wherein the measurement sensor means is at least one of: an accelerometer device, a barometric pressure measuring device, a gyroscope, a sound measuring device, a light measuring device, magnetic field sensing device, and a strain measuring device that includes a strain gage.

15. The device of claim 13 wherein the data indicating the trigger event is data from an accelerometer device.

16. The device of claim 13 wherein the data indicating the trigger event is an acceleration magnitude spike.

17. The device of claim 13 further comprising performing further analysis of the potential fall event data before characterizing the potential fail event data as a fall if the elevation change value exceeds a second elevation change threshold value;

wherein the further analysis includes comparison of at least one of an integral, a mean, a median, an average, a standard deviation, and Fourier analysis result to corresponding integral, mean, median, average, standard deviation, or Fourier analysis result values for characteristic segmentation.

\* \* \* \* \*